(12) United States Patent
Fukuyama et al.

(10) Patent No.: US 7,420,052 B2
(45) Date of Patent: Sep. 2, 2008

(54) INTERMEDIATES FOR SYNTHESIS OF VINBLASTINE, PROCESS FOR PREPARATION OF THE INTERMEDIATES AND PROCESS FOR SYNTHESIS OF VINBLASTINES

(75) Inventors: Tohru Fukuyama, Tokyo (JP); Hidetoshi Tokuyama, Tokyo (JP); Satoshi Yokoshima, Kanagawa (JP)

(73) Assignee: Japan Science and Technology Agency, Saitama-ken (JP)

( * ) Notice: Subject to any disclaimer, the term of this patent is extended or adjusted under 35 U.S.C. 154(b) by 0 days.

(21) Appl. No.: 11/464,560

(22) Filed: Aug. 15, 2006

(65) Prior Publication Data

US 2006/0293357 A1 Dec. 28, 2006

Related U.S. Application Data

(62) Division of application No. 10/486,384, filed as application No. PCT/JP02/08190 on Aug. 9, 2002, now Pat. No. 7,238,802.

(30) Foreign Application Priority Data

Aug. 24, 2001 (JP) .............................. 2001-254108

(51) Int. Cl.
*C07D 487/04* (2006.01)
(52) U.S. Cl. .................................... 540/478
(58) Field of Classification Search ................ 540/478
See application file for complete search history.

(56) References Cited

OTHER PUBLICATIONS

Kuehne et al., Enantioselective Syntheses of Vinblastine, Leurosidine, Vincovaline, and 20'-epi-Vincovaline, Organic Chemistry, vol. 56, No. 2, pp. 513-528, 1991.*
Noble et al., Role of Chance Observations in Chemotherapy: *Vinca rosea*, Annals New York Academy of Sciences, pp. 882-895, 1958.*
Blasko et al., The Alkaloids—Antitumor Bisindole Alkaloids from *Catharanthus roseus* (L.), vol. 37, Academic Press, Inc. San Diego, CA, 1990.*
Kutney et al., Total Synthesis of Indole and Dihydroindole Alkaloids, Helvetica Chimica Acta, vol. 58, Fasc. 6 (1975), pp. 1690-1719.*
von Gottfried Schill et al., Neue Synthese von Vinblastinderivaten: 20'-Deethyl-20'-deoxyvinblastin und 20'-Deethyl-20'-deoxy-C"-homovinblastin, Helvetica Chimica Acta, vol. 69 (1986), pp. 438-441.*
Tokuyama et al., Radical Cyclization of 2-Alkenylthioanilides: A Novel Synthesis of 2,3-Disubstituted Indoles, J. Am. Chem. Soc. 1999, vol. 121, No. 15, pp. 3791-3792.*

Fujiwara et al., Total Synthesis of Lipogrammistin-A: Efficient Macrocyclization with 2-Nitrobenzenesulfonamide, Synlett, 2000, No. 11, pp. 1667-1669.*
Martinelli et al., Dibutyltin Oxide Catalyzed Selective Sulfonylation of alpha-Chelatable Primary Alcohols, Organic Letters, vol. 1, No. 3, 1999, pp. 447-450.*
Yoshida et al., Facile and Practical Methods for the Sulfonylation of Alcohols Using Ts(Ms)Cl and Me2N(CH2)nNMe2 as a Key Base, Synthesis 1999, No. 9, pp. 1633-1636.*
Men et al., A Uniform Numbering System for Indole Alkaloids, Experientia XXI, Breves comunicazioni-Brief Reports, pp. 508-510, 1965.*
Magnus et al., Nonoxidative Coupling Methodology for the Synthesis of the Antitumor Bisindole Alkaloid Vinblastine and a Lower-Half Analogue: Solvent Effect on the Stereochemistry of the Crucial C-15/C-18' Bond, J. Am. Chem. Soc., 1992, vol. 114, No. 26, pp. 10232-10245.*

* cited by examiner

*Primary Examiner*—Brenda L Coleman
(74) *Attorney, Agent, or Firm*—Hahn & Voight; Roger C. Hahn

(57) ABSTRACT

An intermediate for vinblastine synthesis represented by general formula A.

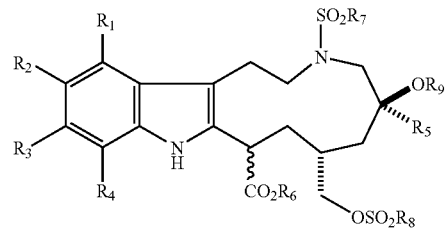

general formula A.
(in the formula, $R_1$, $R_2$, $R_3$ and $R_4$ are the group selected independently from the group consisting of H, lower alkyl group, lower alkoxy group, halogen, lower perfluoroalkyl group, lower alkylthio group, hydroxy group, amino group, mono- or di-alkyl or acylamino group, lower alkyl or arylsulfonyloxy group. $R_5$ is H, or a lower alkyl group or a substituted or non-substituted aryl group, $R_6$ is an alkyl group of carbon number 4 or less, $R_7$ is a substituted or non-substituted aryl group, $R_8$ is a substituted or non-substituted aryl group or lower alkyl group and $R_9$ is an acyl group or trialkylsilyl group.) A method for synthesis of the compound of general formula A utilizing radical ring forming reaction of thioanilides and using the compound of general formula B as the starting material, synthesizing thioanilide of general formula C by the reaction with compound 1 and the formation of a 11-membered ring by intramolecular alkylation of 2-nitrobenzenesulfonamide by which the reactions can proceed under mild conditions and high yield can be accomplished.

1 Claim, No Drawings

INTERMEDIATES FOR SYNTHESIS OF VINBLASTINE, PROCESS FOR PREPARATION OF THE INTERMEDIATES AND PROCESS FOR SYNTHESIS OF VINBLASTINES

CROSS REFERENCE TO RELATED APPLICATIONS

This application is a divisional application of Ser. No. 10/486,384, having a filing or § 371(e) date of Feb. 10, 2004, which is a national stage application of PCT/JP02/08190 dated Aug. 9, 2002, claiming foreign priority to JP 2001/254108 dated Aug. 24, 2001.

FIELD OF THE INVENTION

The present invention relates to an intermediate useful for the synthesis of carbomethoxyvelbanamine unit, which composes one indole ring derivative, useful for the total synthesis of vinblastine, the effective and diversible synthetic method to form said intermediate, and the method for preparation of the analogues of natural vinblastine with high stereoselectivity using said intermediate.

BACKGROUND OF THE INVENTION

It was found that the natural vinblastine (X) which is an alkaloid extracted from catharanthus roseus has a strong cancerocidal effect and currently used as a remedy for vicious lymphoma or ciliary tumor (Reference Document A). Further, aiming the development of novel medicines, various derivatives making vinblastine as a lead compound are investigated and synthesized (Reference Document B). However, in the present conditions, the syntheses of the most of these derivatives depend on partial syntheses from natural vinblastine or analogues thereof. There is a limitation in the chemical transformation of the natural compound, and it is impossible to investigate the wide and systematic structure-activity relationships. For the effective and systematic synthesis of the derivatives, it is necessary to establish the effective total synthesis of vinblastine. Vinblastine (X) can be considered as a bisindole compound generated by bonding two indole units, vindoline and carbomethoxyvelbanamine (Y).

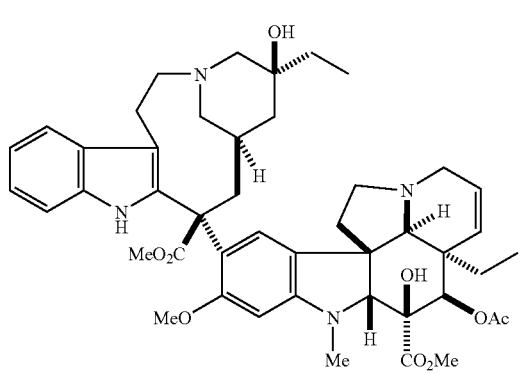

(X)

Therefore, it is important to establish the method for synthesis of each indole unit. However, in the synthesis of the compound composing vindoline unit which is said one compound, the sufficient supplement of vindoline so as to synthesize said vinblastine effectively was not established. In said circumstance, the inventor of the present invention already proposed the effective method for (−)-vindoline (JP application No. 2000-335349 filed on Nov. 7, 2000). Still more, as another problem, the problem that even if the compound (Y) is used as the compound to lead the other indole unit (called as the upper unit) into which vindoline is introduced, sometimes the reaction proceeds with opposite stereoselectivity, is reported (Reference Document C).

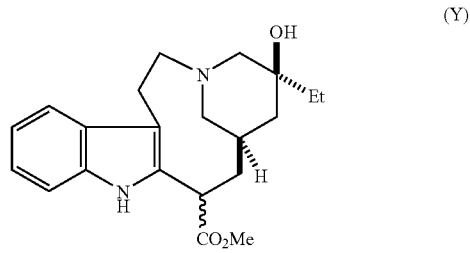

(Y)

Therefore, it is not possible to accomplish the above desired subject, namely, to synthesize vinblastine derivatives effectively, unless the indole derivative which composing the upper unit into which vindoline can be introduced with the desired stereoselectivity is designed and the method for total synthesis of the derivative is established.

Regarding the design of the indole derivative which composing the upper unit, Schill et al reported that vindoline can be introduced with the desired stereoselectivity, when a compound (Z) possessing an eleven-membered ring obtained by ring opening of piperidine ring is used (Reference Document D).

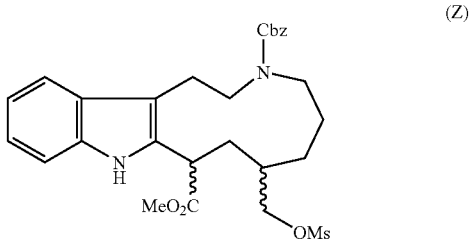

(Z)

However, since the process to obtain the above eleven-membered ring compound is very complicated, the synthesis of vinblastine using compound (Z) is far from an effective synthetic method from the view point of yield.

The subject of the present invention is based on the knowledge of the above mentioned report by Schill et al, and is intending, (1) to establish an effective and highly stereoselective synthetic method of an upper unit, and to provide a method capable of synthesizing the upper unit derivative (2) with high flexibility to synthesize various vinblastine analogous, and (3) where control of the stereochemistry at the introduction of vindoline is improved. For the purpose to accomplish the above mentioned subjects, the inventors of the present invention have tried to combine the method for synthesis of indole (Reference Document E) using a radical ring forming reaction of thioanilide developed by the inventors of the present invention and the method for synthesis of middle and large ring compound (Reference Document F) using intramolecular alkylation of 2-nitrobenzenesulfonamide. In said investigation, it has become clear that the compound which forms said upper unit can be synthesized under relatively mild conditions when above mentioned reactions are used by combination. Therefore, it is possible to make various functional groups coexist in each reactant when these reactions are used by combination, and said basic subjects of (1) and (2) are dissolved.

DISCLOSURE OF THE INVENTION

The first one of the present invention is an intermediate for vinblastine synthesis represented by general formula A.

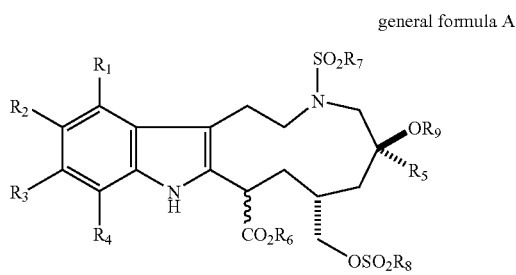

general formula A (in the formula, $R_1$, $R_2$, $R_3$ and $R_4$ are the group selected independently from the group consisting of H, lower alkyl group, lower alkoxy group, halogen, lower perfluoro alkyl group, lower alkylthio group, hydroxyl group, amino group, mono- or di-alkyl or acylamino group, lower alkyl or arylsulfonyloxy group. $R_5$ is H, or a lower alkyl group or a substituted or non-substituted aryl group, $R_6$ is an alkyl group of carbon number 4 or less, $R_7$ is a substituted or non-substituted aryl group, $R_8$ is a substituted or non-substituted aryl group or lower alkyl group and $R_9$ is an acyl group or trialkylsilyl group.)

The second one of the present invention is an intermediate for preparation of the compound of general formula A represented by general formula B.

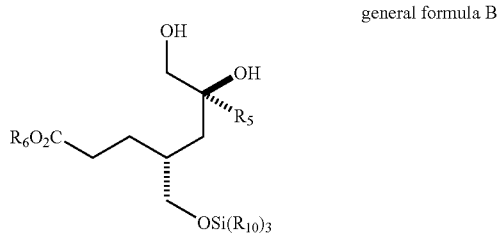

general formula B (in general formula B, $R_5$ and $R_6$ are same as to general formula A. $R_{10}$ is selected independently from the group consisting of alkyl group of carbon number 4 or less and aryl group which can possess a substituent, and three groups selected at each group can be same or different)

The third one of the present invention is an intermediate for preparation of the compound of general formula A represented by general formula C.

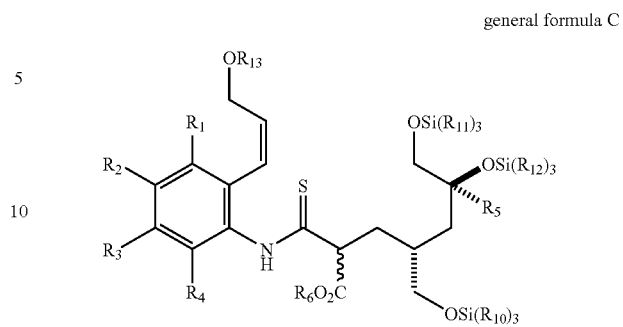

general formula C in general formula C, $R_1$, $R_2$, $R_3$, $R_4$, $R_5$, $R_6$ and $R_{10}$ have same meaning to the case of general formula A and B. $R_{11}$ and $R_{12}$ are selected independently from the group consisting of alkyl group of carbon number 4 or less and aryl group which can possess a substituent, and three groups selected at each group can be same or different. $R_{13}$ is trialkylsilyl group, tetrahydropyranyl group or an acetal structure with other lower alcohol.)

The fourth one of the present invention is an intermediate for preparation of the compound of general formula A represented by general formula D.

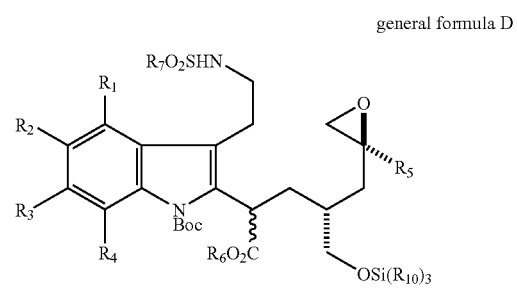

general formula D (in general formula D, $R_1$, $R_2$, $R_3$, $R_4$, $R_5$, $R_6$, $R_7$ and $R_{10}$ have same meaning to the case of general formula A and B. Boc is t-butoxycarbonyl group or H.)

The fifth one of the present invention is the method for synthesis of the compound of general formula A comprising, using the compound of general formula B as the starting material, synthesizing thioanilide of general formula C by the reaction with compound 1 and utilizing radical ring forming reaction of thioanilides.

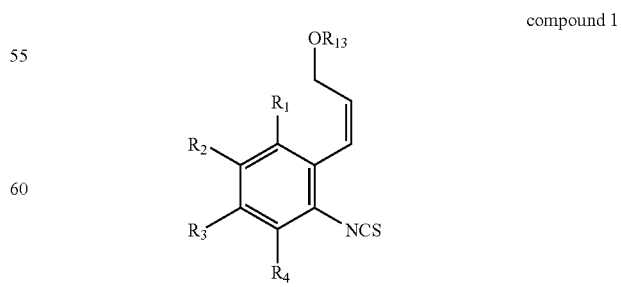

compound 1

(in compound 1, $R_1$, $R_2$, $R_3$, $R_4$ and $R_{13}$ have same meaning to the case of general formula A and C.)

The sixth one of the present invention is the method for preparation of the compound A of claim 1 characterizing to synthesize general formula A using middle ring compound forming reaction of above general formula D.

The seventh one of the present invention is the method for synthesis of (+)-vinblastines represented by general formula F comprising, chlorination of 3 site of indole by treating indole derivatives of general formula A with t-butyl hypochlorite, preparing the compound of general formula E by coupling of vindolines by the treatment of the obtained chlorinated product with trifluoroacetic acid in the presence of vindolines, then removing trifluoroacetyl group and $SO_2R_7$, and forming a piperidine ring.

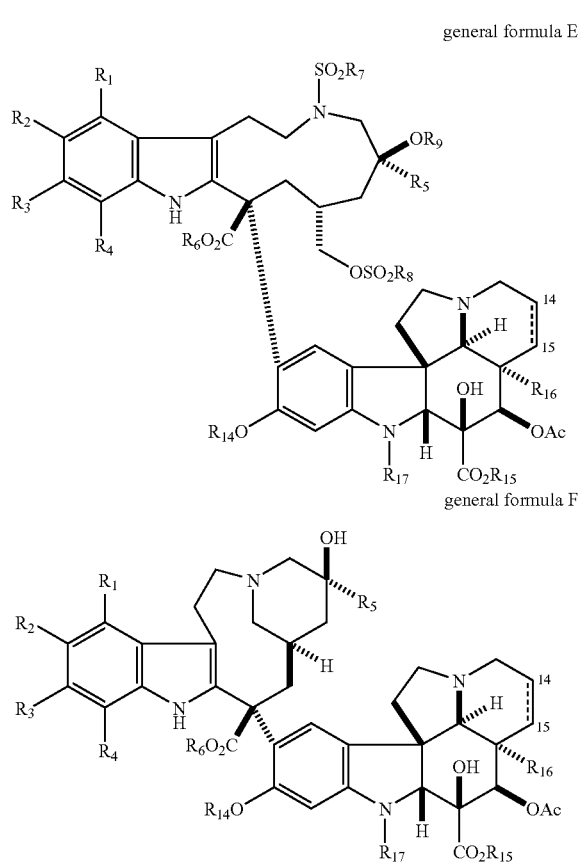

general formula E general formula F

[in general formulae E and F, $R_1$, $R_2$, $R_3$, $R_4$, $R_5$, $R_6$, $R_7$, $R_9$ and $R_9$ have same meaning to the case of general formula A. $R_{14}$, $R_{15}$ and $R_{16}$ are an alkyl group of carbon number 4 or less. $R_{17}$ is H or an alkyl group of carbon number 4 or less. And, carbon 14-carbon 15 is an unsaturated double bond or saturated bond. In this case, the numbering at nomenclature of vindolines is based on the nomenclature method proposed by Men et al (Reference Document J).]

THE BEST EMBODIMENT TO CARRY OUT THE INVENTION

The present invention will be illustrated in more detail according to the following description.

A. The characteristics of the present invention will be illustrated by describing a starting material, intermediate and the preparing method of vinblastine.

1. Thioanilide of general formula C can be synthesized by reacting the compound prepared by protecting two hydroxyl groups of general formula B as silylether and isothiocyanate of compound 1. The process for synthesis is follows. As the desirable group of $R_5$, ethyl group can be mentioned, as the desirable group of $R_5$, methyl group can be mentioned, as the desirable group of $R_{10}$, the combination of t-butyl group and two phenyl groups can be mentioned, as the desirable group of $R_{11}$, ethyl group can be mentioned, as the desirable group of $R_{12}$, methyl group can be mentioned and as the desirable group of $R_{13}$, tetrahydropyranyl group can be mentioned.

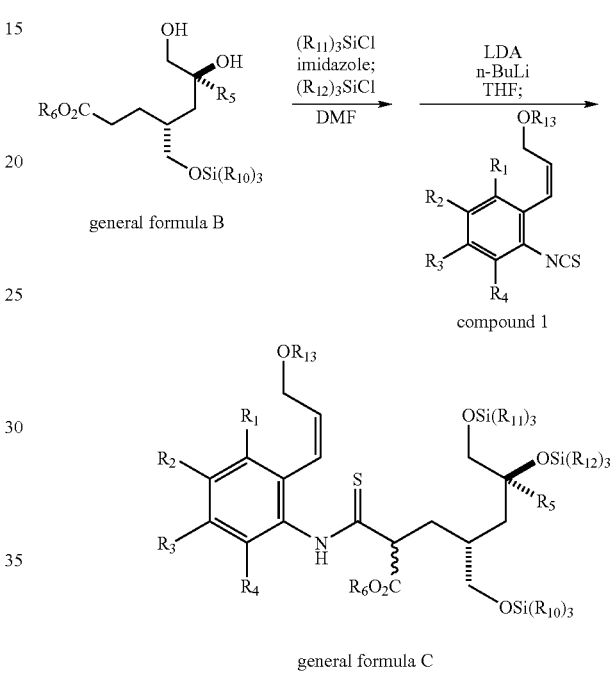

general formula B compound 1 general formula C

2. Thioanilide compound of general formula C is reacted at the room temperature by radical ring forming reaction in THF in which $(Bu)_3SnH$ and $Et_3B$ are existing. The process is shown below. While, it is possible to use toluene, benzene, acetonitrile or dioxane can be used instead of THF. Further, it is possible to use AIBN in toluene or benzene at 80° C. instead of to use Et3B in THF at room temperature. Still further, it is possible to use phosphonic acid, triethylamine and AIBN in n-propanol at 90° C. instead of using $(Bu)_3SnH$ and $Et_3B$ in THF at 80° C.

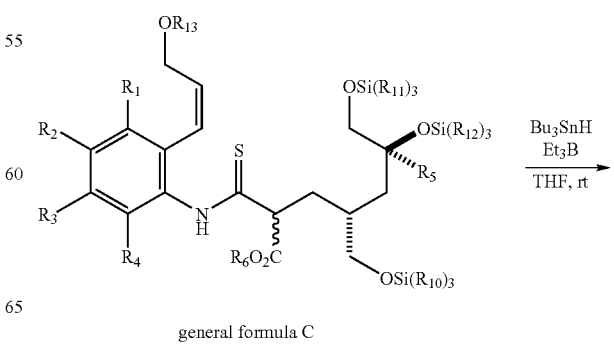

general formula C

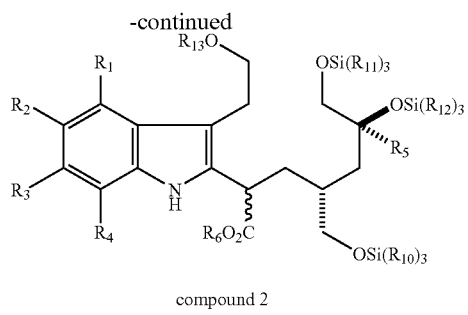

compound 2

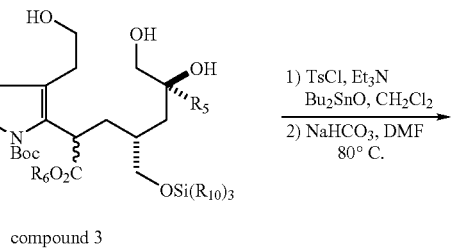

compound 3

3. Then, compound 2 is reacted in $CH_2Cl$ in which $Boc_2O$, Et3N and 4-dimethylaminopyridine (DMAP) are existing at room temperature, and treated with aqueous acetic acid solution at 80° C., further, the compound 3 can be obtained by introduction of a protecting group (Boc) and by deprotection. This process is illustrated by following scheme. In this process, it is possible to use acetonitrile instead of $CH_2Cl_2$. The concentration of aqueous solution of acetic acid can be voluntarily selected, however, the desirable concentration is 95%. Still more, proton acid such as camphorsulfonic acid or p-toluenesulfonic acid in lower alcohol solvent can be used instead of using aqueous solution of acetic acid at 80° C.

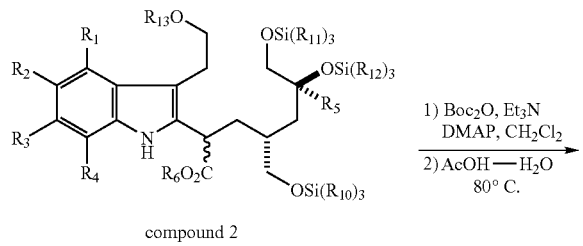

compound 2

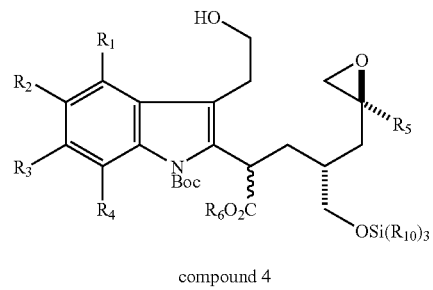

compound 4

5. After that, to the compound 4, sulfone amide is introduced to the remaining primary hydroxyl group by Mitsunobu reaction in toluene in which $R_7SO_2NH_2$, for example, $NsNH_2$, azodicarboxylic acid derivatives for example, diethylazodicarboxylic acid (DEAD) and $Ph_3P$ are existing at the room temperature and the compound represented by general formula D, which is a ring forming precursor, is obtained This process is shown below. The compound intermediate to which sulfonamide is introduced is a key compound to form eleven-membered ring.

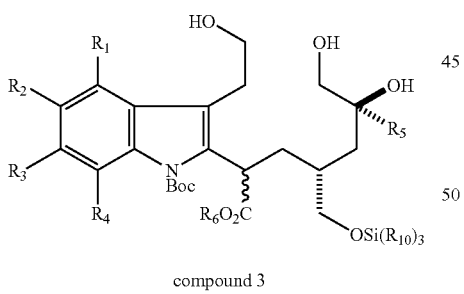

compound 3

4. The process to form eleven-membered ring of said general formula A is carried out as follows, so as to use middle and large ring forming reaction which uses alkylation reaction of Ns amide. Primary hydroxyl group of 1,2-diol of compound 3 is selectively tosylated in $CH_2Cl_2$ solution in which tosylchloride (TsCl), $Bu_2SnO$ and Et3N are existing at the room temperature (Reference Document G), and by heating at 80° C. in DMF in which $MHCO_3$ (wherein M is Na or K) is existing epoxide compound 4 is obtained. This process is shown below. In this process, it is possible to use substituted or non-substituted aryl sulfonyl chloride instead of TsCl.

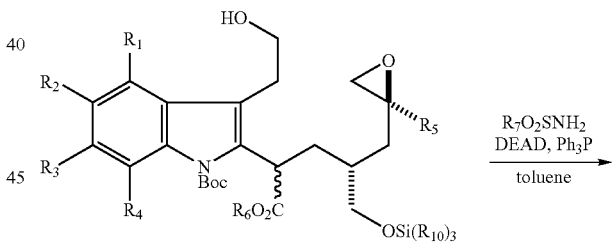

compound 4

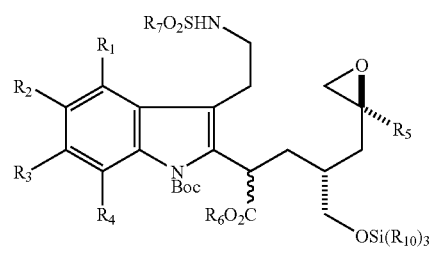

general formula D

6. The compound of general formula D is heated at 90° C. in DMF or acetonitrile in which $M_2CO_3$ (M is Na, K or Cs) is existing so as to proceed middle or large ring forming reaction regioselectively, and eleven-membered ring compound 5 is obtained. The process is shown as follows.

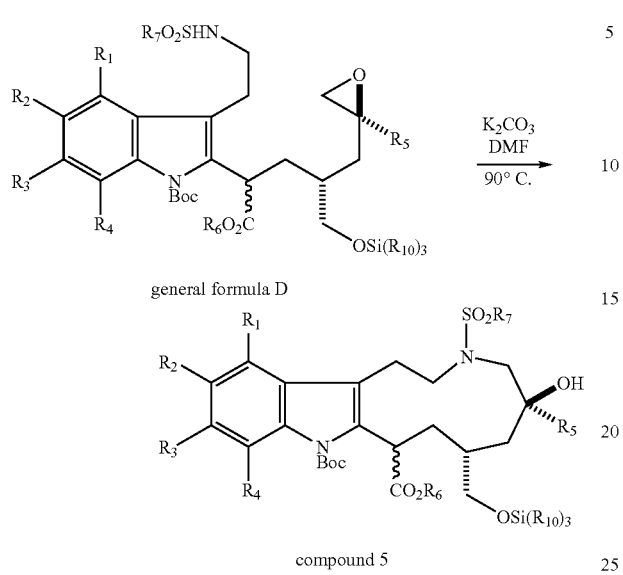

general formula D compound 5

7. Compound 5 is treated by the treating process in CH$_2$Cl$_2$ in which trifluoroacetic acid (TFA) is existing at the room temperature, the treating process in CH$_3$CN-toluene mixed solution in which TsCl and Me$_2$N(CH$_2$)$_3$NMe$_2$ are existing at the room temperature (Reference Document H) and the treating process in CH$_2$Cl$_2$ solution of trifluoroacetic anhydride (TFAA) and pyridine at the room temperature, and the aimed compound A is obtained by deprotection and introduction of a protecting group. The process is shown below. While, it is possible to use substituted or non-substituted aryl sulfonyl chloride instead of TsCl. Further, it is possible to use tertiary amine such as pyridine, triethylamine or diisopropylethylanine instead of Me$_2$N(CH$_2$)$_3$NMe$_2$. Further, the reaction of CH$_3$CN-toluene mixed solution can be changed voluntarily, and CH$_2$Cl$_2$ can be use instead of said mixed solution.

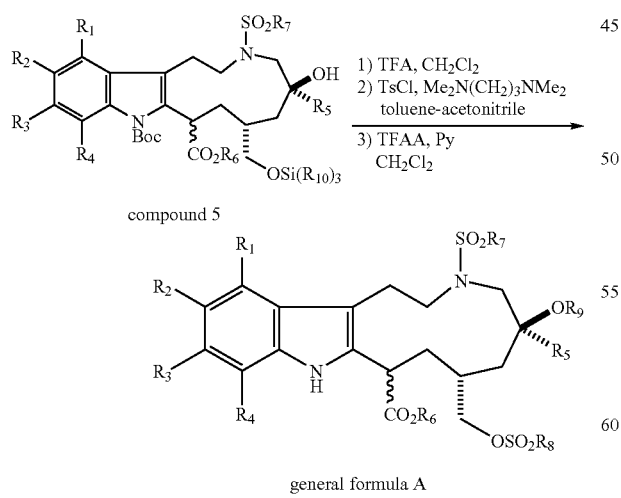

compound 5 general formula A

B. The example for synthesis of the compound represented by general formula B, which is a starting material compound of the present invention, is illustrated as follows.

The reaction process of series is summarized as follows.

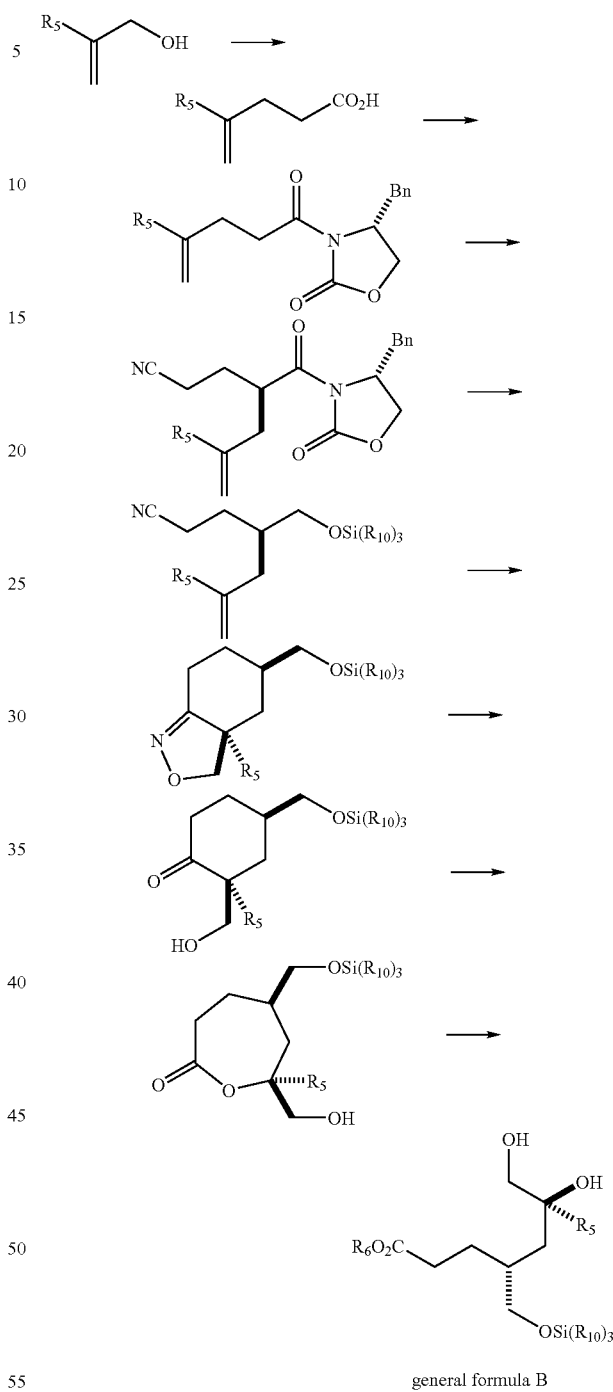

general formula B

EXAMPLE

The present invention will be illustrated more in detail according to the Examples, however, not intending to limit the scope of the claim of the present invention by the Examples.

The synthesis of the compound represented by general formula B, which is the starting material.

Example 1

The process to produce carboxylic acid 2 from the public known starting material 1 is shown as follows.

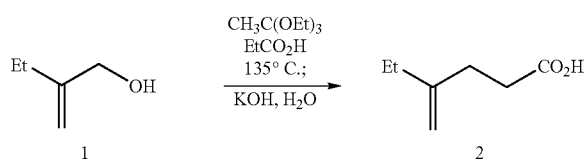

To triethyl orthoacetate solution of alcohol 1 (199.5 g, 2.316 mol), propionic acid (0.86 mL, 11.58 mmol) was added and stirred at 135° C. The generated ethanol was gathered in a dropping funnel attached to a flask. When the generation of ethanol stopped, the reaction mixture was cooled down less than 80° C., and the contain in the dropping funnel was put back into the reaction mixture. The process mentioned above was continued until the alcohol, which was the starting material, was gone.

After consumption of the alcohol, which was the starting material, was confirmed, water (100 ml) was added to the reaction mixture. After stirring for 2 hours and half at room temperature, aqueous solution of potassium hydroxide (390 g, 6.95 mol) was added, cooling with ice and stirred for another 1 hour maintaining the same temperature and continued the stirring for one night at room temperature. The reaction mixture was neutralized with conc. hydrochloric acid, and the organic layer was separated and extracted with dichloromethane and dried over anhydrous magnesium sulfate. After concentration of the solution under the atmospheric pressure, the residue was distilled under reduced pressure, and carboxylic acid 2 (boiling point: from 93 to 96, 247.5 g, 83.38%) was obtained as a colorless liquid.

The characteristics of carboxylic acid 2;
IR (film): 3083, 2968, 1712, 1649, 1438, 1415, 1296, 892 cm$^{-1}$; $^1$HNMR (CDCl$_3$, 400 MHz) 11.63 (brs, 1H), 4.78 (d, J=0, 4 Hz, 1H), 4.73 (d, J=0, 4 Hz, 1H), 2.52 (t, J=7.7 Hz, 2H), 2.36 (t, J=7.7 Hz, 2H), 2.05 (q, J=7.2 Hz, 2H), 1.04 (t, J=7.2 Hz, 3H); $^{13}$CNMR (CDCl$_3$, 100 MHz) 180.2, 149.4, 108.3, 32.6, 30.7, 29.0, 12.3; analysis; calculated value (Anal. Calcd for) C$_7$H$_{12}$O: C, 65.60, H, 9.44; analytical result (found) C, 65.50, H, 9.37.

The process to produce imide 3 from carboxylic acid 2 is shown below.

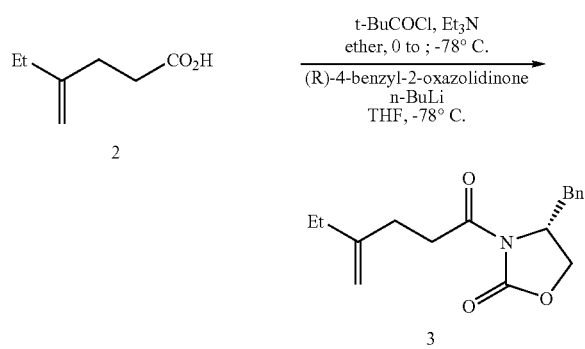

To diethyl ether solution (1 L) of carboxylic acid 2 (28.20 g, 220.0 mmol) and triethylamine (30.66 ml, 220.0 mmol), which was cooled with ice, pivaloyl chroride (26.93 mL, 220.0 mmol) was dropped. Maintaining the same temperature, the reaction mixture was stirred for 40 minutes, and then cooled down to −78° C. (mixed anhydride diethyl ether solution). While, to tetrahydrofuran solution (500 mL) of oxazolidinone (35.44 g, 200 mmol), n-butyllithium (2.46M n-hexane solution, 81.3 mL, 200 mmol) was dropped at −78° C. This solution was dropped to the mixed anhydride diethyl ether solution using a canular. After dropping the reaction mixture was stirred for 50 minutes at −78° C. and for another 30 minutes at 0° C. Then the saturated aqueous solution of sodium bicarbonate was added to the reaction mixture so as to separate organic layer and extracted with ethyl acetate. The organic layer was combined, washed with brine, and then dried over anhydrous magnesium sulfate. After concentration in vacuo, the residue was purified by a silica gel column chromatography, and imide 3 (51.0 g, 88.7%) was obtained as a colorless oily product.

The characteristics of imide 3:
$[\alpha]^{26}_D$-52.0 (c1.15, CHCl$_3$); IR (film) 3029, 2966, 2921, 1783, 1701, 1648, 1454, 1388, 1353, 1212, 1110, 892, 762, 743, 703 cm$^{-1}$; $^1$HNMR (CDCl$_3$, 400 MHz) 7.33 (t, J=7.0 Hz, 2H), 7.27 (t, J=7.0 Hz, 1H), 7.20 (d, J=7.0 Hz, 2H), 4.79 (d, J=1.1 Hz, 1H), 4.77 (d, J=1.1 Hz, 1H), 4.67 (ddt, J=9.8, 8.3, 3.3, 3.2 Hz, 1H), 4.19 (dd, J=9.0, 8.3 Hz, 1H), 4.15 (dd, J=9.0, 3.2 Hz, 1H), 3-29 (dd, J=13.5, 3.2 Hz, 1H), 3.14 (ddd, J=17.0, 8.4, 7.2 Hz, 1H), 2.76 (dd, J=13.5, 9.8 Hz, 1H), 2.42 (m, 2H), 2.09 (q, J=7.3 Hz, 2H), 1.06 (t, J=7.3 Hz, 3H);
$^{13}$CNMR (CDCl$_3$, 100 MHz) 172.9, 153.4, 149.6, 135.3, 129.4, 128.9, 127.3, 108.4, 66.2, 55.2, 37.9, 34.0, 30.4, 29.0, 12.3.

The process to produce adduct 4 from imide 3 is shown below.

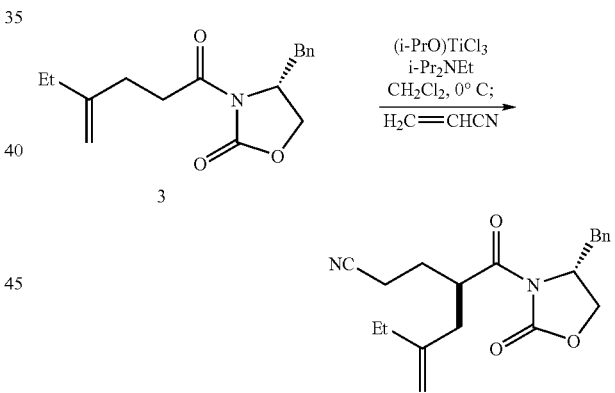

Titanium tetrachloride (16.0 mL, 145.5 mmol) was dropped into dichloromethane solution (265 mL) of titanium tetraisopropoxide (14.4 mL, 48.5 mmol). This solution was dropped into dichloromethane solution (176 mL) of imide 3 (50.7 g, 176 mmol) and diisopropylethylamide (45.8 mL, 265 mmol), which was cooled with ice, and stirred for 40 minutes maintaining the same temperature. Acrylonitrile (34.8 mL, 529 mmol) was dropped to the reaction mixture and further stirred for 9 hours and half at the same temperature. Saturated ammonium chloride aqueous solution was added to the reaction mixture so as to separate the organic layer, and then extracted with ethyl acetate. The organic layer was combined, washed with saturated sodium bicarbonate and brine, and then dried over anhydrous magnesium sulfate. After concentration in vacuo, the residue was purified by a silica gel column chromatography (5-12% ethyl acetate/n-hexane), and adduct 4 (42.3 g, 70.4%) was obtained as a colorless oily product.

The characteristics of adduct 4:

$[\alpha]^{26}_D$ −36.4 (c0.978, CHCl$_3$); IR (film) 3029, 2967, 2935, 2247, 1779, 1695, 1646, 1453, 1389, 1351, 1291, 1211, 1113, 1014, 902, 762, 742, 703 cm$^{-1}$; $^1$HNMR(CDCl$_3$, 400 MHz) 7.35 (t, J=7.0 Hz, 2H), 7.29 (t, J=7.0 Hz, 1H), 7.22 (d, J=7.0 Hz, 2H), 4.83 (d, J=1.4 Hz, 1H), 4.75 (d, J=1.4 Hz, 1H), 4.65 (m, 1H), 4.19 (m, 2H), 4.09 (ddt, J=12.0, 7.3, 4.4 Hz, 1H), 3.34 (dd, J=13.4, 3.4 Hz, 1H), 2.78 (dd, J=13.4, 10.0 Hz, 1H), 2.49 (dd, J=14.0, 7.0 Hz, 1H), 2.38 (m, 2H), 2.15 (dd, J=14.0, 7.6 Hz, 1H), 2.08 (m, 1H), 2.04 (q, J=7.3 Hz, 1H), 1.90 (m, 1H), 1.03 (t, J=7.3 Hz, 3H); $^{13}$CNMR(CDCl$_3$, 100 MHz) 174.7, 153.1, 147.6, 135.2, 129.4, 129.0, 127.4, 119.1, 110.9, 66.4, 55.6, 40.5, 39.0, 38.1, 28.3, 27.1, 15.1, 12.2;

The process to produce alcohol 5 from adduct 4 is shown below.

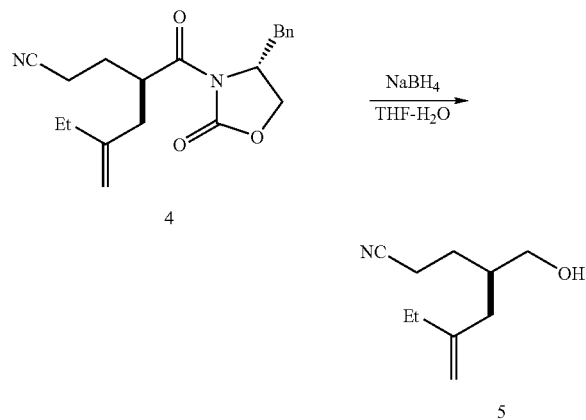

Sodium borohydride (22.6 g, 597.4 mmol) was dissolved in water (150 mL) and dropped into tetrahydrofuran solution (300 mL) of adduct 4 (50.84 g, 149.3 mmol), which was cooled with ice The temperature was elevated to the room temperature and stirred for one night. The reaction mixture was cooled down with ice, hydrochloric acid was added so as to adjust the pH to 5, and then extracted with ethyl acetate 3 times. The organic layer was combined, then washed with diluted hydrochloric acid, saturated aqueous solution of sodium bicarbonate and brine and dried over anhydrous magnesium sulfate. After concentration in vacuo, the residue was refined by a silica gel column chromatography (25-35% ethyl acetate/n-hexane), and alcohol 5 (22.9 g, 91.7%) is obtained as a colorless oily product.

The characteristics of alcohol 5:

$[\alpha]^{27}_D$ −1.56 (c0.960, CHCl$_3$); IR (film) 3449, 3078, 2965, 2931, 2249, 1644, 1450, 1328, 1037, 984, 895 cm$^{-1}$; $^1$HNMR (CDCl$_3$, 400 MHz) 4.84 (d, J=1.5 Hz, 1H), 4.77 (d, J=1.5 Hz, 1H), 3.64 (dd, J=10.9, 4.4 Hz, 1H), 3.55 (dd, J=10.9, 5.4 Hz, 1H), 2.46 (t, J=7.3 Hz, 2H), 2.13 (dd, J=14.0, 7.7 Hz, 1H), 2.03 (q, J=7.4 Hz, 2H), 2.02 (dd, J=14.0, 7.8 Hz, 1H), 1.87 (m, 1H), 1.74 (m, 2H), 1.05 (t, J=7.4 Hz, 3H); $^{13}$CNMR(CDCl$_3$, 100 MHz) 148.6, 120.0, 110.3, 64.4, 38.2, 37.0, 28.1, 27.0, 15.0, 12.1;

The process to produce silylether 6 from alcohol 5 is shown below.

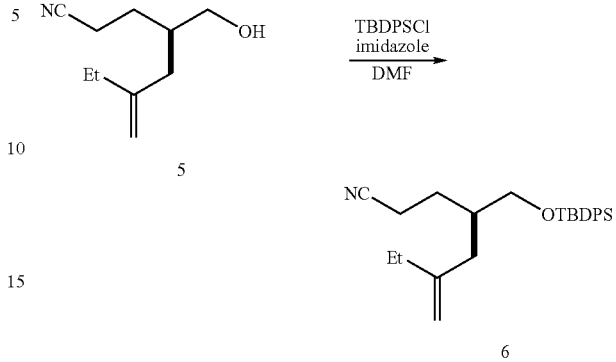

To a dimethylformamide solution (136 mL) of alcohol 5 (22.8 g, 136.3 mmol) and imidazole (13.92 g, 204.5 mmol), t-butylchlorodiphenylsilane (39.0 mL) was dropped at room temperature, and stirred for 1 hour at room temperature. The reaction mixture was diluted with diethyl ether, and washed with water. The aqueous layer was extracted with diethyl ether, and then the combined organic layer was washed with water and brine and dried over anhydrous magnesium sulfate. After concentration in vacuo, the residue was refined by a silica gel column chromatography (0-2% ethyl acetate/n-hexane), and silyl ether 6 (50.6 g, 91.5%) was obtained as a colorless oily product.

The characteristics of silylether 6;

$[\alpha]^{23}_D$ +6.49 (c1.99, CHCl$_3$); IR (film) 3071, 2961, 2931, 2858, 2246, 1644, 1589, 1471, 1428, 1112, 1083, 894, 823, 741, 703, 614, 505 cm$^{-1}$; $^1$HNMR (CDCl$_3$, 400 MHz) 7.64 (d, J=7.3 Hz, 4H), 7.44 (t, J=7.3 Hz, 2H), 7.39 (t, J=7.3 Hz, 4H), 4.76 (d, J=1.4 Hz, 1H), 4.67 (d, J=1.4 Hz, 1H), 3.56 (dd, J=9.4, 3.4 Hz, 1H), 3.53 (dd, J=9.4, 4.2 Hz, 1H), 2.30 (ddd, J=16.8, 8.3, 6.3 Hz, 1H), 2.23 (dd, J=16.8, 7.3 Hz, 1H), 2.15 (dd, J=13.9, 6.6 Hz, 1H), 1.94 (dd, J=13.9, 7.6 Hz, 1H), 1.93 (q, J=7.3 Hz, 2H), 1.79 m, 1H), 1.74 (m, 2H), 1.06 (s, 9H), 0.99 (t, J=7.3 Hz, 3H); $^{13}$CNMR (CDCl$_3$, 100 MHz) 148.5, 135.6, 135.6, 133.4, 133.4, 129.8, 129.8, 127.8, 127.7, 120.0, 110.3, 65.3, 38.2, 37.4, 28.2, 27.2, 26.9, 19.3, 15.0, 12.0;

The process to produce isoxazoline 7 from silylether 6 is mentioned below.

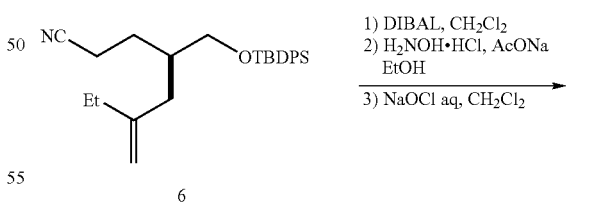

To a dichloromethane solution (90 mL) of silyl ether (32.8 g, 80.9 mmol) diisobutylaluminum hydride (DIBAL) (1.0M toluene solution, 88.9 mL, 88.9 mmol) was dropped at −78°

C. and stirred for 20 minutes. Dichloromethane solution of acetic acid (20 mL) was added to the reaction mixture and the temperature was elevated to room temperature. After partition between ethyl acetate and dilute hydrochloric acid, the aqueous layer was extracted with ethyl acetate. The combined organic layer was washed with dilute hydrochloric acid, saturated aqueous solution of sodium bicarbonate and brine, and then dried over anhydrous magnesium sulfate. After concentration in vacuo, into the solution of the residue in ethanol (120 mL), sodium acetate (13.27 g, 161.7 mmol) and hydroxylamine hydrochloride (8.43 g, 121.3 mmol) were added, and the resulting suspension was stirred for 1 hour at room temperature. Saturated aqueous solution of sodium bicarbonate was added to the solution and extracted with ethyl acetate, and then the combined organic layer was washed with saturated brine. After dryness over anhydrous sodium sulfate, the solution was concentrated in vacuo. After the residue was dissolved in dichloromethane (404 mL), aqueous solution of sodium hypochlorite (approximately 5%, 190 mL) was dropped at room temperature and stirred for 3 hours and half. Cooling with ice, sodium sulfite was added to the reacted solution and stirred for several minutes, and then the organic layer was separated. After extraction of the aqueous layer with ethyl acetate, the combined organic layer was washed with brine and dried over anhydrous sodium sulfate. After concentration in vacuo, the residue was refined by a silica gel column chromatography (5-8% ethyl acetate/n-hexane), and isoxazoline 7 (20.0 g, 58.7%) was obtained as a colorless oily product.

The characteristics of isoxazoline 7;

$[\alpha]^{25}_D$+8.5 (c2.06, CHCl$_3$); IR (film) 3070, 2931, 2858, 1471, 1428, 1388, 1112, 1063, 846, 823, 741, 704, 614 cm$^{-1}$; $^1$HNMR (CDCl$_3$, 400 MHz) 7.63 (d, J=7.4 Hz, 4H), 7.44 (t, J=7.4 Hz, 2H), 7.38 (t, J=7.4 Hz, 4H), 4.27 (d, J=8.0 Hz, 1H), 3.77 (d, J=8.0 Hz, 1H), 3.52 (dd, J=9.3, 5.4 Hz, 1H), 3.48 (dd, J=9.3, 5.5 Hz, 1H), 2.67 (ddd, J=13.9, 4.9, 2.2 Hz, 1H), 2.15 (td, J=13.9, 5.4 Hz, 1H), 2.08 (dt, J=13.0, 2.4 Hz, 1H), 2.02 (m, 1H), 1.88 (m, 1H), 1.67 (dq, J=14.1, 7.5 Hz, 1H), 1.49 (dq, J=14.1, 7.5 Hz, 1H), 1.20 (t, J=13.0 Hz, 1H), 1.18 (qd, J=13.9, 4.9 Hz, 1H), 1.05 (s, 9H), 0.89 (t, J=7.5 Hz, 3H); $^{13}$CNMR (CDCl$_3$, 100 MHz) 162.5, 135.5, 135.5, 133.6, 133.5, 1129.7, 129.7, 127.6, 127.6, 79.0, 68.0, 55.1, 39.1, 35.7, 29.5, 26.8, 26.4, 22.0, 19.2, 8.3;

The process to produce hydroxyketone 8 from isoxazoline 7 is mentioned below.

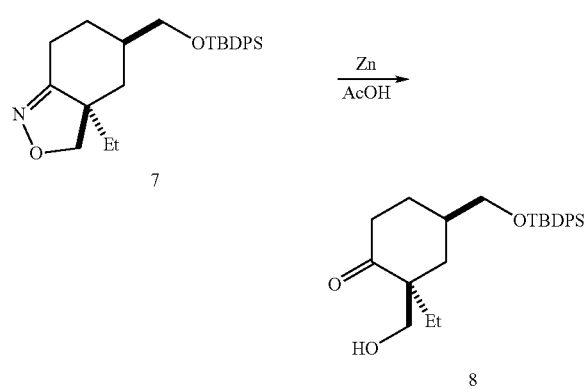

The acetic acid suspension (165 mL) of isoxazoline 7 (17.4 g, 41.3 mmol) and zinc dust (27.0 g, 413 mmol) was stirred at room temperature for 4 hours. After the reaction mixture was diluted with dichloromethane, zinc dust was removed using Celite column. Saturated aqueous solution of sodium bicarbonate was added to the solution, which was neutralized by adding solid sodium bicarbonate. After the organic layer was separated, the aqueous layer was extracted with dichloromethane. The combined organic layer was washed with water, and dried over anhydrous sodium sulfate. After concentration in vacuo, the residue was refined by a silica gel column chromatography (10-15% ethyl acetate/n-hexane), and hydroxylketone 8 (11.6 g, 66.4%) was obtained as a light yellowish oily product.

The characteristics of hydroxyl ketone 8;

$[\alpha]^{26}_D$+54.4 (c1.40, CHCl$_3$); IR (film) 3489, 3070, 2981, 2858, 1699, 1471, 1427, 1389, 1191, 1112, 1056, 997, 823, 741, 703, 614, 506 cm$^{-1}$; $^1$HNMR(CDCl$_3$, 400 MHz) 7.65 (d, J=7.4 Hz, 4H), 7.44 (t, J=7.4 Hz, 2H), 7.39 (t, J=7.4 Hz, 4H), 3.67 (dd, J=11.5, 7.3 Hz, 1H), 3.55 (dd, J=8.8, 4.9 Hz, 1H), 3.51 (dd, J=8.8, 5.2 Hz, 1H), 3.33 (dd, J=11.5, 6.8 Hz, 1H), 2.51 (td, J=14.6, 6.6 Hz, 1H), 2.48 (dd, J=7.3, 6.8 Hz, 1H), 2.28 (ddd, J=14.6, 4.6, 2.4 Hz, 1H), 2.12 (m, 2H), 1.83 (dq, J=15.4, 7.6 Hz, 1H), 1.75 (dq, J=15.0, 3.9 Hz, 1H), 1.52 (dq, J=15.4, 7.6 Hz, 1H), 1.38 t, J=15.0 Hz, 1H), 1.32 (cq, J=14.6, 3.7 Hz, 1H), 1.06 (s, 9H), 0.84 (t, J=7.6 Hz, 3H); $^{13}$CNMR (CDCl$_3$, 100 MHz) 218.5, 135.6, 135.6, 133.7, 133.6, 129.7, 129.7, 127.7, 127.768.1, 65.9, 52.6, 38.3, 34.8, 34.4, 29.5, 26.9, 25.4, 19.3, 7.7;

The process to produce diol 9 from hydroxyketone 8 is mentioned below.

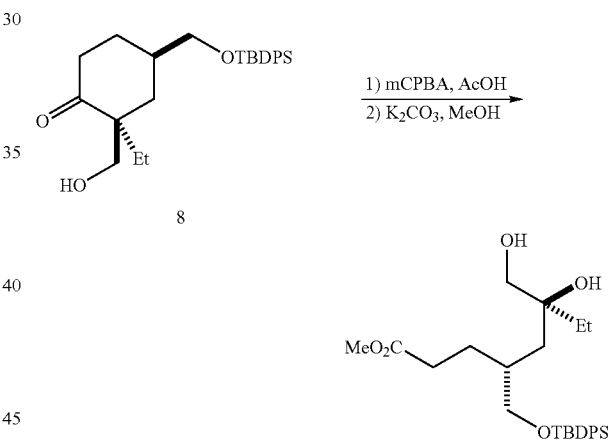

The acetic acid solution (62.8 mL) of hydroxylketone 8 (10.66 g, 25.10 mmol), m-chloroperoxybenzoic acid (mCPBA) (17.32 g, 75.29 mmol) was stirred at room temperature for 41 hours. Cooling with ice, dimethyl sulfide (5.53 mL, 75.3 mmol) was added to the solution, which was stirred for 20 minutes, and then concentrated in vacuo. The residue was dissolved in ethyl acetate, which was washed with sodium bicarbonate and brine and dried over anhydrous sodium sulfate. After concentration in vacuo, the residue was dissolved in methanol (77 mL) and potassium carbonate (382 g, 27.6 mmol) was added and stirred at room temperature for 45 minutes. After the solution was diluted with diethyl ether, the organic layer was separated, and then the aqueous layer was extracted with ethyl acetate. The combined organic layer was washed with brine, then the residue was refined by a silica gel column chromatography (20-40% ethyl acetate/n-hexane), and diol 9 (9.49 g, 80.0%) was obtained as a light yellowish oily product.

The characteristics of diol 9;

[α]$^{27}_{D+}$10.0 (c1.50, CHCl$_3$); IR (film) 3441, 3071, 2932, 2859, 1738, 1462, 1428, 1362, 1172, 1112, 1071, 823, 741, 704, 614, 504 cm$^{-1}$; $^1$HNMR(CDCl$_3$, 400 MHz) 7.67 (m, 4H), 7.43 (t, J=6.7 Hz, 2H), 7.40 (t, J=6.7 Hz, 4H), 3.64 (s, 3H), 3.57 (dd, J=10.0, 4.6 Hz, 1H), 3.51 (s, 1H), 3.46 (brs, 2H), 3.42 (dd, J=10.0, 7.7 Hz, 0H), 2.23 (t, J=7.4 Hz, 2H), 2.09 (m, 1H), 1.82 (m, 1H), 1.63-1.48 (m, 9H), 1.06 (s, 9H), 0.88 (t, J=7.6 Hz, 3H); $^{13}$CNMR (CDCl$_3$, 100 MHz) 174.4, 135.7, 135.6, 132.9, 132.9, 129.9, 129.9, 127.8, 127.8, 74.0, 68.4, 67.5, 51.6, 38.5, 35.2, 31.4, 30.2, 28.1, 26.8, 19.1, 8.1;

The process to produce aimed silyl ether 10 from diol 9 is mentioned below.

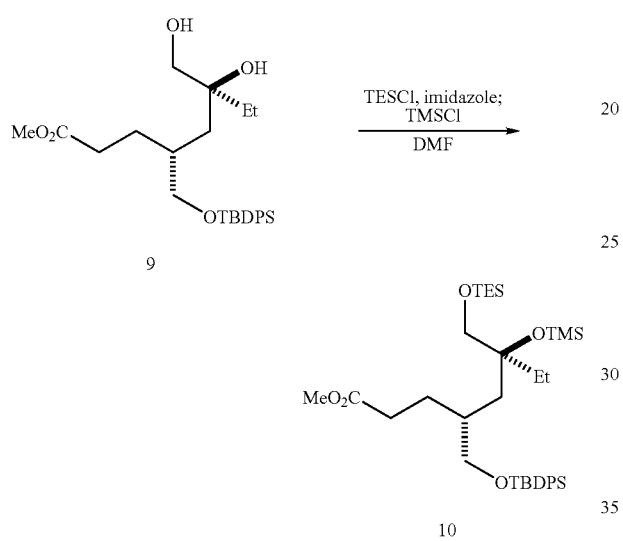

To the dimethylformamide solution (23.4 mL) of diol 9 (5.532 g, 11.70 mmol) and imidazole (2.39 g, 35.11 mmol), chlorotriethylsilane (TESCl) (2.35 ml, 14.0 mmol) was added at room temperature and stirred for 1 hour. After confirmation of disappearance of the starting material, chlorotrimethylsilane (1.78 ml, 14.0 mmol) was added to the reaction mixture and stirred for another 40 minutes. After the reaction mixture was partitioned between diethyl ether and water, the aqueous layer was extracted with diethyl ether. The combined organic layer was washed with brine, and then dried over anhydrous magnesium sulfate. After concentration in vacuo, the residue was refined by a silica gel column chromatography (0-2% ethyl acetate/n-hexane), and silyl ether 10 (7.13 g, 92.4%) was obtained as a colorless oily product.

The characteristics of silyl ether 9;

[α]$^{28}_{D}$-3.48 (c 1.04, CHCl$_3$); IR (film) 2955, 2878, 1742, 1461, 1430, 1249, 1168, 1109, 1011, 839, 741, 704, 612 cm$^{-1}$; $^1$HNMR (CDCl$_3$, 400 MHz) 7.66 (d, J=6.7 Hz, 4H), 7.41 (t, J=6.7 Hz, 2H), 7.36 (t, J=6.7 Hz, 4H), 3.65 (s, 3H), 3.63 (dd, J=10.0, 4.4 Hz, 1H), 3.47 (dd, J=10.0, 6.1 Hz, 1H), 3.41 (d, J=9.8 Hz, 1H), 3.37 (d, J=9.8 Hz, 1H), 2.27 (dd, J=9.0, 7.3 Hz, 1H), 1.81 (m, 3H), 1.55 (m, 2H), 1.41 (dq, J=13.9, 7.4 Hz, 1H), 1.25 (dd, J=14.4, 4.9 Hz, 1H), 1.05 (s, 9H), 0.95 (t, J=7.9 Hz, 9H), 9.77 (t, J=7.4 Hz, 3H), 0.59 (q, J=7.9 Hz, 6H), 9.01 (s, 9H);

$^{13}$CNMR (CDCl$_3$, 100 MHz) 174.6, 135.7, 133.9, 129.5, 127.6, 79.2, 68.0, 67.0, 51.4, 36.9, 35.5, 31.7, 31.6, 29.9, 27.8, 26.9, 8.3, 6.9, 4.4, 2.6;

II The synthesis of the compound contained in general formulae C, D and A, The characteristics of silylether 9;

Example 2 a. Synthesis of thioanilide 12 contained in general formula C from isothiocyanate 11 corresponding to the compound wherein all of R$_1$-R$_4$ in above mentioned silylether 10 and compound 1 are H. The process for synthesis is illustrated below.

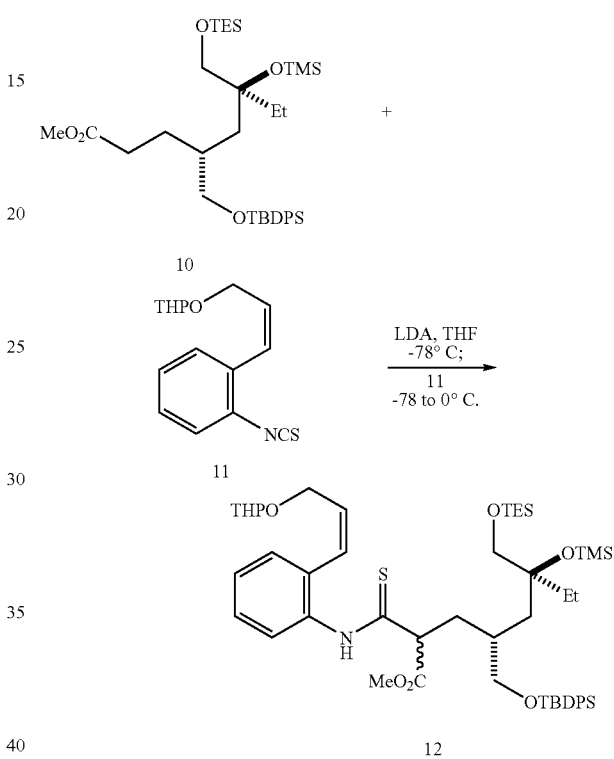

To a tetrahydrofuran (THF) solution (40.5 ml) of diisopropylamine (3.17 ml, 22.5 mmol) n-butyllithium (hexane solution of 1.46M, 19.7 mmol) was dropped by cooling with ice, stirred for 10 minutes, then cooled down to −78° C. Tetrahydrofuran solution (40.5 mL) of silyl ether 10 (9.268 g, 14.06 mmol) was dropped and stirred for 1 hour keeping said temperature. Tetrahydrofuran solution (15 mL) of isothiocyanate 11 (3.872 g, 14.06 mmol) was dropped to the reaction mixture. Stirred for 50 minutes at said temperature, then the temperature was elevated to 0° C. and further stirred for 15 minutes. After dilution with diethyl ether, saturated aqueous solution of ammonium chloride was added. The organic layer was separated, and then the aqueous layer was extracted with ethyl acetate. The combined organic layer was washed with brine and dried over anhydrous sodium sulfate. After concentration in vacuo, the residue was refined by a silica gel column chromatography (5-10% ethyl acetate/n-hexane), and thioanilide 12 (9.95 g, 75.7%) was obtained as a yellowish oily product.

The characteristics of thioanilide 12;

$^1$HNMR (CDCl$_3$, 400 MHz) 9.78 (s, (¼)1H), 9.74 (s, (¼) 1H), 9.63 (s, (¼) 1H), 9.60 (s, (¼)1H), 7.83 (d, J=7.8 Hz, 1H), 7.67 (m, 5H), 9.38 (m, 8H), 6.50 (d, J=11.5 Hz, 1H), 6.00 (ddd, J=11.5, 6.4, 3.9 Hz, 1H), 4.60 (t, J=3.4 Hz, 1H), 3.43 (ddd, J=12.7, 5.8, 1.9 Hz, 1H), 4.16 (m, (½) 1H), 4.09 (ddd, J=12.7, 7.1, 1.6 Hz, 1H), 4.03 (m, (½) 1H), 3.81 (m, 2H), 3.74 (s, 3H), 3.57 (m, 1H), 3.49-3.40 (m, 3H), 2.24 M, 2H), 1.93 (m (½) 1H), 1.82 (m, 1H+(½)1H), 1.68 (m, 2H), 1.53 (m, 4H), 1.44-1.20 (m, 3H), 1.07 (s, (½) 9H), 1.05 (s, (112) 9H), 0.94 (t, J=7.9 Hz, 9H), 0.79 (t, J=7.3 Hz, (½) 3H), 0.77 (t, J=7.3 Hz, (½) 3H), 0.59 (q, J=7.9 Hz, (½) 6H), 0.58 (q, J=7.9 Hz, (½) 6H), 0.01 (s, (½) 9H), 0.00 (s, (½) 9H);

The process to produce indole compound 13 contained in above mentioned compound 2 by radical ring forming reaction of thioanilide 12 is mentioned below.

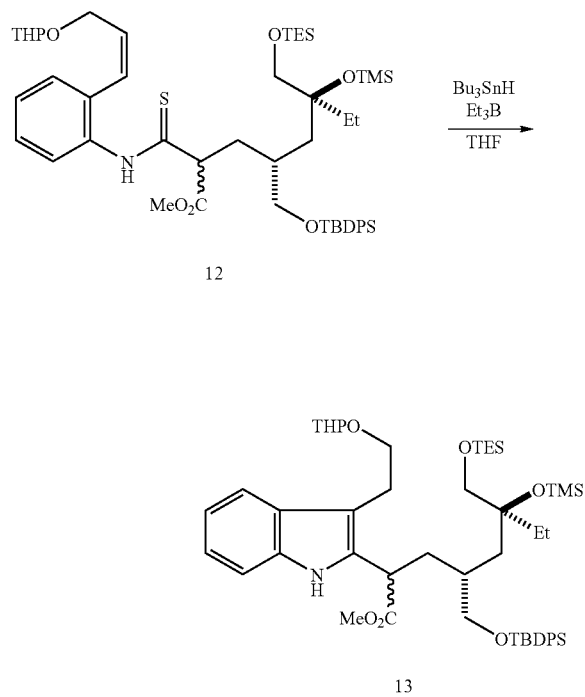

To a tetrahydrofuran solution of thioanilide 12 (8.628 g, 9.233 mmol), tributyltin hydride (4.97 ml, 18.47 mmol), triethylborane (1.0M hexane solution, 1.85 ml, 1.85 mmol) was dropped at room temperature and stirred for 1 hour. Saturated sodium bicarbonate aqueous solution is added to the reaction mixture and extracted three times with ethyl acetate. The combined organic layer was washed with brine, and dried over anhydrous sodium sulfate. After concentration in vacuo, the residue was refined by a silica gel column chromatography (2-8% ethyl acetate/n-hexane), and indole 13 (5.51 g, 66.1%) was obtained as an yellowish oily product.

The characteristics of indole 13;

$^1$HNMR (CDCl$_3$, 400 MHz) 8.68 (s, (¼) 1H), 8.65 (s, (¼) 1H), 8.39 (s, (½) 1H), 7.61 (m, 6H), 7.37 (m, 6H), 7.12 (m1H), 7.06 (m, 1H), 4.54 (m, (½) 1H), 4.51 (m, (½) 1H), 4.12 (m, 1H), 3.96 (m, 1H), 3.83 (m, 1H), 3.66 (s, (½ 3H), 3.63 (s, (½) 3H), 3.50 (m, 3H), 3.39 (m, 3H), 3.31 (m 1H), 2.96 (m, 2H), 2.85 (m, 1H), 2.33 (m, 1H), 2.23 (m, 1H), 2.13 (m, 1H), 1.79 (m, 2H), 1.60-1.37 (m, 4H), 1.27 (m, 2H), 1.06 (s, (½) 9H), 1.05 (s, (½) 9H), 0.99-0.81 (m, 9H), 0.74 (t, J=7.2 HzH (½) 3H, 0.67 (t, J=7.2 Hz, (¼) 3H), 0.66 (t, J=7.2 Hz, (¼) 3H), 0.56 (m, 6H), 0.11 (s, (¼) 9H), 0.10 (s, (¼) 9H), 0.00 (s, (¼) 9H), −0.01 (s, (¼) 9H;

The compound 14 to which protecting group is introduced from indole 13 can be obtained by following process.

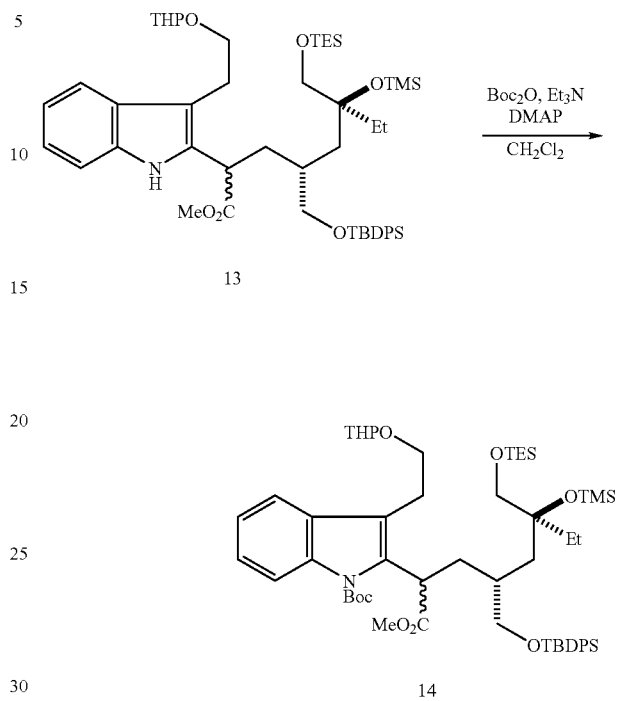

To a dichloromethane solution (16.8 mL) of indole 13 (6.055 g, 6.709 mmol) and triethylamine (1.40 mL, 10.1 mmol), Boc$_2$O (2.93 g, 13.4 mmol) and 4-dimethylaminopyridine (82 mg, 0.67 mmol) were added and stirred for one night at room temperature. Water was added to the reaction mixture and the organic layer was separated, then the aqueous layer was extracted with ethyl acetate. The combined organic layer was washed with brine, and then dried over anhydrous magnesium sulfate. After concentration in vacuo, the residue was refined by a silica gel column chromatography (3-8% ethyl acetate/n-hexane), and silyl ether compound 14 (5.83 g, 86.7%) was obtained as an yellowish oily product.

The characteristics of silyl ether compound 14;

$^1$HNMR (CDCl$_3$, 400 MHz) 7.95 (m, 1H), 7.67 (m, 3H), 7.53 (t, J=8.3 Hz, 2H), 7.37 (m, 6H), 7.21 (m, 2H), 4.57 (m, 1H), 4.51 (m, 1H), 4.23 (m, (½) 1H), 4.12 (m, (½) 1H), 3.92 (m, (½) 1H), 3.85 (m, (½) 1H), 3.82 (m, 1H), 3.70 (m, 1H), 3.60 (s, (½) 3H), 3.59 (s, (¼) 3H), 3.58 (s, (¼) 311), 3.57 (m, 2H), 3.43 (m, 3H), 3.19 (m, 2H), 2.92 (m, 2H), 2.82 (m, 2H), 2.53 (m, (½) 1H), 2.12 (m, (½) 1H), 1.86 (m, 1H), 1.64 (s, (¼) 9H), 1.60 (s, (¼) 9H), 1.57 (s, (½) 9H), 1.72-1.40 (m, 4H), 1.28 (m, 2H), 1.27 (brs, (½) 9H), 1.06 (s, (½) 9H), 0.93 (t, J=8.0 Hz, (¼) 9H), 0.89 (t, J=8.0 Hz, (¼) 9H), 0.85 (t, J=8.0 Hz, (¼) 9H), 0.84 (t, J=8.0 Hz, (¼) 9H), 0.74 (t, J=7.2 Hz, (½) 3H), 0.65 (t, J=7.2 Hz, (½) 3H), 0.56 (q, J=8.0 Hz, (½) 6H), 0.45 (q, J=8.0 Hz, (¼) 6H), 0.44 (q, J=8.0 Hz, (¼) 6H), −0.03 (s, (½) 9H), −0.10 (s, (¼) 9H), −0.11 (s, (¼) 9H;

The process to produce triol compound 15 contained is above mentioned compound 3 from silylether 14 is mentioned below.

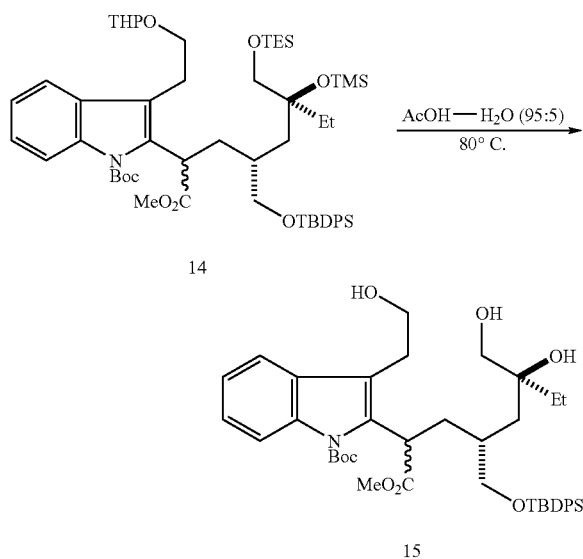

14

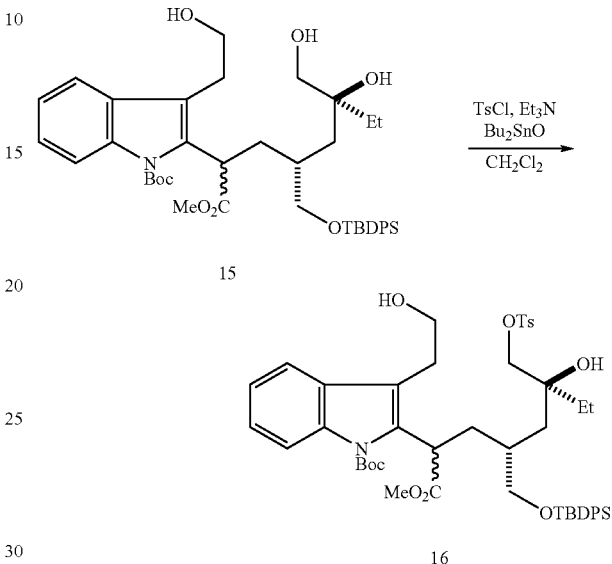

15

The acetic acid-water (95:5) solution (7.4 mL) of silyl ether compound 14 (184 mg, 0.184 mmol) was stirred for 30 minutes at 80° C. After concentration in vacuo, the residue was refined by a silica gel column chromatography (20-80% ethyl acetate/n-hexane), and triol 15 (101 g, 75%) was obtained as an light yellowish oily product.

Isomers were separated with silica gel thin layer chromatography, and the instrument date was measured.

The characteristics of triol 14;

I. Less Polar Isomer

[α] $^{26}_{D+}$ $^{78}$ (c 0.57, CHCl$_3$); IR (film) 3423, 2934, 2860, 1731, 1457, 1431, 1366, 1325, 1231, 1163, 1131, 1113, 1047, 910, 823, 738, 705, 614 cm$^{-1}$; $^1$HNMR (CDCl$_3$, 400 MHz) 7.96 (d, J=7.8 Hz, 1H), 7.65 (d, J=7.8 Hz, 2H), 7.62 (d, J=7.7 Hz, 2H) 7.44 (m, 3H), 7.37 (m, 3H), 7.30 (td, J=7.8, 1.2 Hz, 1H), 7.23 (dd, J=7.8, 2 Hz, 1H), 4.05 (t, J=6.3 Hz, 1H), 3.74 (m, 1H), 3.68z8m, 1H), 3.61 (s, 3H), 3.60 (dd, J=9.9, 4.9 Hz, 1H), 3.36 (dd, J=9.9, 7.9 Hz, 1H), 3.28 (s, 2H), 2.82 (dt, J=14.4, 4.3 Hz 1H), 2.67 (ddd, J=14.4, 9.0, 5.6 Hz, 1H), 2.42 (dt, J=13.7, 6.3 Hz, 1H), 1.87 (m, 1H), 1.79 (ddd, J=13.7, 7.3, 5.6 Hz, 1H), 1.63 (s, 9H), 1.62 (dd, J=15.0, 5.9 Hz, 1H), 1.50 (dd, J=15.0, 4.3 Hz, 1H), 1.34 (q, J=7.6 Hz, 2H), 1.03 (s, 9H), 0.75 (t, J=7.6 Hz, 3H); $^{13}$CNMR(CDCl$_3$, 100 MHz) 173.2, 150.4, 135.8, 135.7, 135.6, 135.5, 132.9, 132.8, 129.9, 129.8, 129.1, 127.8, 127.8, 124.6, 122.7, 118.6, 117.8, 115.9, 84.4, 73.8, 68.6, 67.2, 61.7, 52.2, 41.3, 38.6, 34.1, 34.0, 30.0, 28.2, 27.7, 26.8, 19.1, 7.8;

II. More Polar Isomer

[α] $^{26.5}_{D}$–59 (c0.47, CHCl$_3$); IR (film) 3430, 2934, 2863, 1728, 1458, 1430, 1366, 1362, 1230, 1163, 1131, 1116, 1048, 910, 738, 705, 614 cm$^{-1}$; $^1$HNMR(CDCl$_3$, 400 MHz) 7.93 (d, J=8.0 Hz, 1H), 7.61 (d, J=8.1 Hz, 2H), 7.58 (d, J=8.1 Hz, 2H), 7.42 (t, J=8.0 Hz, 1H), 7.39 (t, J=8.1 Hz, 2H), 7.32 (t, J=8.1 Hz, 4H), 7.26 (dd, J=8.0, 1.0 Hz, 1H), 7.23 (td, J=8.0, 1.0 Hz, 1H), 3.96 (brs, 1H), 3.66 (m, 2H), 3.63 (s, 3H), 3.55 (dd, J=10.2, 2 Hz, 1H), 3.51 (d. J=11.0 Hz, 1H), 3.47 (d, J=11.0 Hz, 1H), 3.37 (dd, J=10.2, 8.4 Hz, 1H), 2.74 (dt, J=14.4, 4.7 Hz, 1H), 2.58 (ddd, J=14.4, 8.3, 6.4 Hz, 1H), 2.47 (ddd, J=14.7, 6.8, 5.1 Hz, 1H), 1.98 (m, 1H), 1.68 (dd, J=14.9, 5.9 Hz, 1H), 1.61 (dd, J=14.9, 7.1 Hz, 1H), 1.60 (m, 2H), 1.60 (s, 9H), 1.45 (ddd, J=14.7, 7.6, 4.9 Hz, 1H), 0.98 (s, 9H), 0.91 (t, J=7.4 Hz, 3H); $^{13}$CNMR(CDCl$_3$, 100 MHz) 173.5, 150.3, 135.8, 135.6, 135.6, 135.6, 132.9, 132.8, 129.8, 129.8, 129.2, 127.8, 127.7, 124.5, 122.7, 118.6, 116.9, 115.9, 84.4, 74.2, 68.9, 67.6, 61.8, 52.3, 42.0, 39.2, 35.6, 34.9, 30.2, 28.1, 27.7, 26.7, 19.0, 8.2;

The process to produce tosylate 16 from triol compound 15 is mentioned below.

To a dichloromethane suspension (2 mL) of triol 15 (148 mg, 0.202 mmol), triethylamine (84 μL, 0.606 mmol) and dibutyltin oxide (15 mg, 0.061 mmol), p-toluenesulfonyl chloride (40 mg, 0.212 mmol) was added and stirred at room temperature for 20 hours. After the solid was removed using Celite column, the filtrate was concentrated in vacuo. The residue was refined by a silica gel column chromatography (25-40% ethyl acetate/n-hexane), and tosylate 16 (149 g, 83.2%) was obtained as a light yellowish oily product.

Isomers were separated by silica gel thin film chromatography, and the instrument date was measured.

The characteristics of tosilate 16;

I. Less Polar Isomer

[α] $^{24}_{D}$+73 (c 0.41, CHCl$_3$); IR (film) 3543, 3397, 2934, 1731, 1597, 1457, 1431, 1364, 1325, 1253, 1232, 1175, 1130, 1113, 1044, 973, 911, 842, 821, 740, 705, 667, 615, 555 cm$^{-1}$; $^1$HNMR (CDCl$_3$, 400 MHz) 7.96 (d, J=8.3 Hz, 1H), 7.68 (d, J=8.1 Hz, 2H), 7.50 (m, 5H), 7.39 (m, 2H), 7.32 (td, J=7.3, 1.2 Hz, 1H), 7.29 (t, J=7.3 Hz, 4H), 7.26 (dd, J=7.3, 1.2 Hz, 1H) 7.23 (d, J=8.1 Hz, 2H), 3.96 (brs, 1H), 3.93 (d, J=9.2 Hz, 1H), 3.79 (d, J=9.2 Hz, 1H), 3.69 (m, 2H), 3.63 (s, 3H), 3.47 (dd, J=10.3, 3.8 Hz, 1H), 3.33 (dd, J=10.3, 8.3 Hz, 1H), 2.90 (dt, J=14.4, 4.5 Hz, 1H), 2.65 (ddd, J=14.4, 9.0, 6.1 Hz, 1H), 2.41 (ddd, J=15.9, 6.1, 4.6 Hz, 1H), 2.37 (s, 2H), 1.83 (m, 1H), 1.69 (dd, J=14.9, 4.4 Hz, 1H), 1.61 (m, 1H), 1.58 (s, 9H), 1.51 (m, 1H), 1.00 (m, 2H), 0.91 (s, 9H), 0.79 (t, J=7.6 Hz, 3H); $^{13}$CNMR(CDCl$_3$, 100 MHz) 173.2, 150.3, 144.7, 135.7, 135.5, 135.5, 135.4, 132.6, 132.5, 132.5, 129.9, 129.8, 129.8, 129.3, 128.0, 127.8, 127.8, 124.5, 122.7, 118.8, 117.5, 116.0, 84.4, 73.1, 72.4, 68.9, 61.8, 52.3, 41.8, 40.2, 35.3, 34.7, 30.5, 28.1, 27.8, 26.7, 21.6, 19.0, 7.5;

II. More Polar Isomer

[α] $^{25}_{D}$–20 (c 0.57, CHCl$_3$); IR (film) 3416, 2934, 1729, 1597, 1457, 1431, 1364, 1325, 1254, 1231, 1175, 1131, 1112, 1045, 974, 912, 841, 821, 739, 705, 667, 614, 556, 508 cm$^{-1}$; $^1$HNMR (CDCl$_3$, 400 MHz), 7.96 (d, J=7.6 Hz, 1H), 7.68 (d, J=8.3 Hz, 2H), 7.61 (m, 4H), 7.47 (t, J=7.6 Hz, 1H), 7.43 (m, 2H), 7.37 (m, 4H), 7.29 (td, J=7.6, 1.2 Hz, 1H), 7.26 (d, J=8.3 Hz, 2H), 7.23 (dd, J=7.6, 2 Hz, 1H), 3.98 (t, J=5.5 Hz, 1H), 3.82 (d, J=9.3 Hz, 1H), 3.74 (m, 2H), 3.64 (d, J=9.3 Hz, 1H), 3.63 (dd, J=10.0, 2.3 Hz, 1H), 3.61 (s, 3H), 3.33 (dd, J=10.0, 8.3 Hz, 1H), 2.92 (dt, J=14.2, 5.2 Hz, 1H), 2.72 (dt, J=14.2, 8.0 Hz, 1H), 2.41 (s, 2H), 2.40 (m, 1H), 1.98 (m, 1H), 1.65 (m, 1H), 1.61 (s, 9H), 1.58 (m, 2H), 1.37 (dq, J=14.4, 7.4 Hz, 1H), 1.31 (dq, J=14.4, 7.4 Hz, 1H), 1.00 (s, 9H), 0.68 (t, J=7.4 Hz, 3H); $^{13}$CNMR(CDCl$_3$, 100 MHz) 172.9, 150.3, 144.9, 135.8, 135.7, 135.6, 135.6, 132.5, 132.5, 132.5, 132.4, 130.0, 129.9, 129.3, 128.0, 127.9, 127.8, 124.4, 122.6, 118.6, 117.4, 116.0, 84.3, 72.9, 72.0, 68.8, 61.8, 52.1, 41.2, 39.4, 34.5, 34.2, 30.5, 28.1, 28.0, 26.8, 21.6, 19.1, 7.3;

The process to produce epoxide 17 which is contained in above mentioned compound 4 from tosylate 16 is mentioned below.

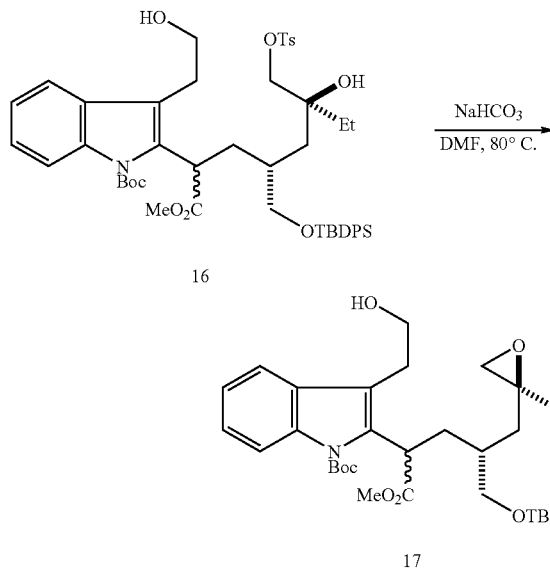

16

17

A dimethylformamide suspension (2.7 mL) of tosylate 17 (238 mg, 0.269 mmol) and sodium bicarbonate (113 mg, 1.343 mmol) was stirred for 2 hours and half at 90° C. To the reaction mixture, saturated sodium bicarbonate aqueous solution was added, and extracted with diethyl ether three times. The combined organic layer was washed with brine and dried over anhydrous magnesium sulfate. After concentration in vacuo, the residue was refined by a silica gel column chromatography (25-40% ethyl acetate/n-hexane), and epoxide 17 (176 g, 91.8%) was obtained as a white solid foam.

Isomers were separated by silica gel thin layer chromatography, and the instrument date was measured.

The characteristics of epoxide 17;

I. Less Polar Isomer

[α]$^{23}_D$+93 (c 0.31, CHCl$_3$); IR (film) 3456, 2934, 2859, 1731, 1588, 1458, 1431, 1364, 1324, 1254, 1229, 1164, 1130, 1113, 1049, 1004, 910, 822, 741, 705, 616 cm$^{-1}$; $^1$HNMR (CDCl$_3$, 400 MHz) 7.98 (d, J=7.7 Hz, 1H), 7.64 (m, 4H), 7.43 (m, 3H), 7.36 (m, 4H), 7.29 (td, J=7.7, 1.2 Hz, 1H), 7.23 (td, J=7.7, 1.2 Hz, 1H), 4.01 (dd, J=9.9, 4.3 Hz, 1H), 3.68 (m, 2H), 3.66 (s, 3H), 3.55 (dd, J=10.2, 4.1 Hz, 1H), 3.47 (dd, J=10.2, 4.7 Hz, 1H), 2.82 (dt, J=14.7, 3.9 Hz, 1H), 2.55 (m, 2H), 2.34 (d, J=4.7 Hz, 1H), 2.27 (d, J=4.7 Hz, 1H), 2.11 (dd, J=9.6, 3.8 Hz, 1H), 2.05 (ddd, J=14.7, 9.8, 3.4 Hz, 1H), 1.66 (m 1H), 1.65 (s, 9H), 1.44 (brs, 1H), 1.21 (qd, J=7.4, 3.6 Hz, 2H), 1.05 (s, 9H), 0.64 (t, J=7.4 Hz, 3H);
$^{13}$CHMR (CDCl$_3$, 100 MHz) 173.0, 150.3, 136.0, 135.8, 135.6, 135.1, 133.5, 133.5, 129.8, 129.7, 129.7, 127.7, 127.7, 124.5, 122.7, 118.5, 118.3, 116.0, 84.4, 65.9, 61.7, 58.7, 52.1, 51.6, 41.8, 36.2, 35.0, 31.8, 28.2, 27.8, 26.9, 26.5, 19.3, 8.5;

II. More Polar Isomer

[α]$^{24}_D$−62 (c 0.36, CHCl$_3$); IR (film) 3455, 2934, 2859, 1730, 1458, 1431, 1365, 1325, 1253, 1229, 1164, 1130, 1112, 1079, 1008, 910, 823, 742, 705, 615 cm$^{-1}$; $^1$HNMR (CDCl$^3$, 400 MHz) 7.99 (d, J=7.8 Hz, 1H), 7.56 (d, J=8.0 Hz, 4H), 7.50-7.20 (m, 9H), 4.14 (t, J=6.8 Hz, 1H), 3.76 (m, 2H), 3.65 (s, 3H), 3.47 (d, J=4.6 Hz, 2H), 2.93 (dt, J=14.4, 4.3 Hz, 1H), 2.80 (ddd, J=14.4, 9.0, 5.9 Hz, 1H), 2.45 (ddd, J=14.2, 6.8, 4.6 Hz, 1H), 2.42 (d, J=4.6 Hz, 1H), 2.40 (d, J=4.6 Hz, 1H), 2.27 (dd, J=9.5, 4.4 Hz, 1H), 2.09 (ddd, J=14.2, 7.3, 4.9 Hz, 1H), 1.63 (s, 9H), 1.62 (m, 1H), 1.39 (m, 2H), 1.06 (m, 1H), 0.90 (s, 9H), 0.76 (t, J=7.6 Hz, 3H); $^{13}$CNMR (CDCl$_3$, 100 MHz) 173.2, 150.4, 135.9, 135.8, 135.6, 135.6, 133.6, 133.4, 129.6, 129.6, 129.3, 127.6, 127.5, 124.5, 122.7, 118.5, 117.6, 116.1, 84.4, 66.7, 61.9, 59.1, 52.3, 52.2, 41.7, 36.3, 36.0, 33.6, 28.1, 28.1, 26.8, 265.7, 19.1, 8.7;

The process to synthesize nosyl amide 18 contained in general formula D by introducing sulfonamide into epoxide 17 is mentioned below.

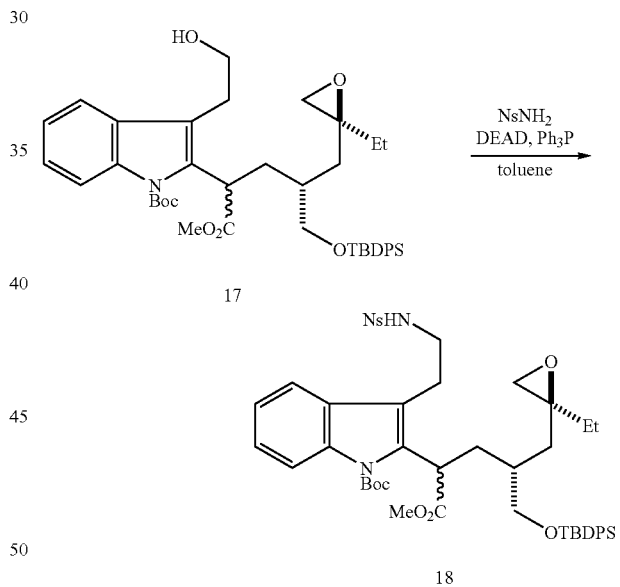

17

18

To a toluene suspension of epoxide 17 (171 mg, 0.240 mmol), 2-nitrobenzene sulfonamide (97 mg, 0.48 mmol) and triphenylphosphine (94 mg, 0.36 mmol), diethyl azodicarboxylate (40% toluene solution, 0.163 mL, 0.358 mmol) was dropped at room temperature, and stirred for 20 minutes. After concentration the residue was refined by a silica gel column chromatography (20-22.5% ethyl acetate/n-hexane), and nosyl amide 18 (187 g, 86.9%) was obtained as a yellowish solid foam.

The characteristics of nocylamide 18;

IR (film) cm$^{-1}$; $^1$HNMR (CDCl$_3$, 400 MHz) 8.04 (dd, J=8.0, 4.0 Hz, (½) 1H), 7.97 (dd, J=6.8, 4.0 Hz, (½) 1H), 7.94 (d, J=8.8 Hz, (½) 1H), 7.91 (d, J=8.0 Hz, (½) 1H), 7.70-7.50 (m, 6H), 7.46-7.36 (m 5H), 7.34-7.32 (m 2H), 7.23-7.17 (m, 2H+ (½) 1H), 7.13 (d, J=6.8 Hz, (½) 1H), 7.09 (t, J=7.4 Hz, (½) 1H), 7.00 (t, J=7.2 Hz, (½) 1H), 5.73 (dd, J=6.8, 4.0 Hz, (½) 1H), 5.48 (dd, J=6.8, 2.8 Hz, (½) 1H), 4.07 (m, (½) 1H), 3.87 (m, (½)1H), 3.71 (s, (½) 3H), 3.68 (s, (½) 3H), 3.53 (dd, J=10.8, 4.8 Hz, (½) 1H), 3.47-3.32 (m, 2H), 3.24 (m, 1H), 2.95 (m, (½) 1H), 2.92 (ddd, J=14.8, 5.6, 4.0 Hz, (½) 1H), 2.84 (dd, J=16.8, 8.0 Hz, (½) 1H), 2.75 (dt, J=14.8, 4.8 Hz, (½) 1H), 2.59 (ddd, J=14.8, 10.0, 4.8 Hz, (½) 1H)<2.48 (d, J=4.8 Hz, (½) 1H), 2.44 (m, 2H), 2.42 (d, J=4.8 Hz, (½) 1H), 2.36 (d, J=4.0 Hz, (½) 1H), 2.30 (d, J=4.0 Hz, (½) 1H), 2.05 (m, 1H), 1.67 (s, (½) 1H), 1.64 (s, (½) 1H), 1.62 (m, 1H), 1.45 (m, 1H), 1.27 (m, 2H), 1.05 (s, (½) 9H), 0.88 (s, (½) 9H)<0.74 (t, J=7.8 Hz, (½) 3H), 0.54 (t, J=7.8 Hz, (½) 3H);

The process to synthesize 11-membered ring compound 19 contained in above mentioned compound 5 by proceeding middle ring forming reaction of nosyl amide 18 is mentioned below.

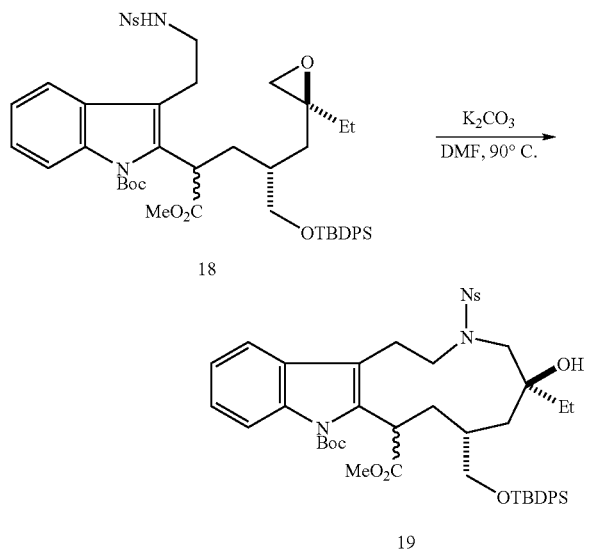

The suspension of nosyl amide 18 (113 mg, 0.126 mmol) and potassium carbonate (35 mg, 0.25 mmol) was stirred for 13 hours at 90° C. After cooled down to the room temperature, saturated aqueous solution of ammonium chloride was added to the reaction mixture, which was extracted with diethyl ether 3 times. The combined organic layer was washed with water and brine, then dried over anhydrous sodium sulfate. The residue was refined by a silica gel column chromatography (25-40% ethyl acetate/n-hexane), and 11-members ring compound 19 (80 mg, 71%) was obtained as a yellowish solid foam.

The characteristics of 11-members ring compound 19;

IR (film) 3397, 3071, 2934, 2859, 1731, 1546, 1459, 1432, 1367, 1327, 1235, 1165, 1115, 910, 735, 705, 581 cm$^{-1}$; $^1$HNMR (CDCl$_3$, 400 MHz) 8.04 (d, J=8.3 Hz, 1H), 7.93 (m, (½) 1H), 7.89 (d, J=7.1 Hz, (½) 1H), 7.78-7.16 (m, 13H+ (½) 1H), 7.13 (d, J=7.3 Hz, (½) 1H), 7.11 (d, J=7.3 Hz, (½) 1H), 6.77 (brs, (½) 3H), 4.83 (s, (½) 1H), 4.31 (brs, (½) 1H), 4.23 (m, (½) 2H), 3.82-3.19 (m, 4H+(½) 1H)<3.60 (s, (½) 3H), 3.56 (s, (½) 3H), 3.12 (m, (½) 1H), 2.98 (m, 1H), 2.88 (d, J=14.9 Hz, (½) 1H), 2.75 (m, (½) 1H), 2.51-1.71 (m, 3H), 1.64 (s, (½) 9H), 1.61 (s, (½) 9H), 1.42-1.15 (m, 4H), 1.06 (s, (½) 9H), 0.98 (s, (½) 9H), 0.89 (t, J=7.6 Hz, (½) 3H), 0.68 (t, J=7.6 Hz, (½) 3H;

The process to synthesize diol 20 possessing 11-membered ring by deprotection of 11-members ring compound 19 is mentioned below.

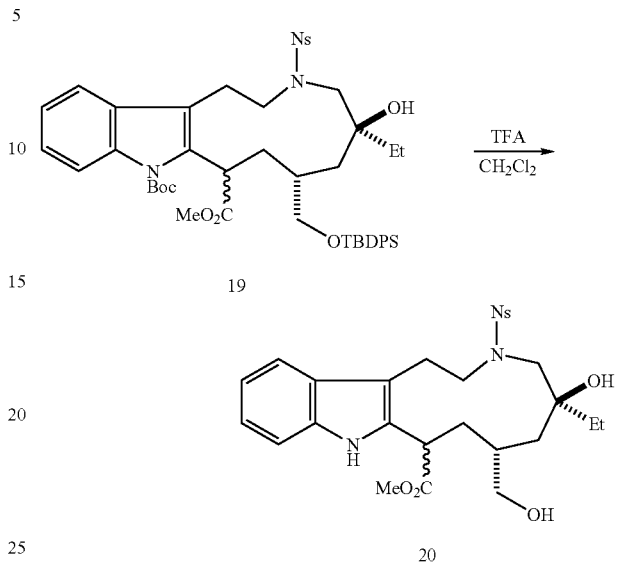

To a dichloromethane solution (2 mL) of 11-membered ring compound 19 (124 mg, 0.138 mmol), trifluoroacetic acid (2 mL) is added at room temperature and stirred for 2 hours. After concentration in vacuo, the residue was dissolved in methanol, into which triethylamine (0.2 mL) was added, and the resulting solution was stirred at room temperature. After concentration in vacuo, the residue was refined by a silica gel column chromatography (50-100% ethyl acetate/n-hexane), and diol 20 (71 mg, 92%) was obtained as an yellowish oily product.

Isomers were separated by silica gel thin layer chromatography, and the instrument date was measured.

The characteristics of diol 20;

I. Less Polar Isomer

[α] $^{22}{}_D$ –89 (c 0.37, CHCl$_3$); IR (film) 3389, 2947, 1728, 1545, 1460, 1439, 1370, 1341, 1167, 910, 734, 580 cm$^-$; $^1$HNMR (CDCl$_3$, 400 MHz) 8.76 (s, 1H), 7-93 (dd, J=7.6, 1.2 Hz, 1H), 7.72 (td, J=7.6, 1.2 Hz, 1H), 7.67 (td, J=7.6, 1.2 Hz, 1H), 7.62 (dd, J=7.6, 1.2 Hz, 1H), 7.42 (d, J=8.0 Hz, 1H), 7.31 (d, J=8.0 Hz, 1H), 7.15 (td, J=8.0, 1.0 Hz, 1H), 7.05 (td, J=8.0, 1.0 Hz, 1H), 4.17 (dd, J=12.8, 3.3 Hz, 1H), 4.07 (ddd, J=15.1, 8.5, 6.6 Hz, 1H), 3.74 (s, 3H), 3.58 (d, J=14.4 Hz, 1H), 3.51 (dd, J=10.9, 4.0 Hz, 1H), 3.46 (dd, J=10.9, 6.3 Hz, 1H), 3.40 (dt, J=15.1, 7.9 Hz, 1H), 3.11 (m, 2H), 3.10 (d, J=14.4 Hz, 1H), 2.97 (ddd, J=15.4, 6.6, 3.3 Hz, 1H), 2.19 (d, J=15.4 Hz, 1H), 2.10 (t, J=12.1 Hz, 1H), 1.77-1.63 (m, 4H), 0.98 (t, J=7.4 Hz, 3H); $^{13}$CNMR (CDCl$_3$, 100 MHz) 174.3, 148.9, 136.0, 133.9, 131.5, 131.3, 130.5, 129.8, 127.2, 124.2, 122.5, 119.8, 118.6, 112.6, 111.2, 74.3, 68.3, 60.4, 53.6, 52.6, 39.4, 37.9, 37.2, 33.7, 33.6, 26.4, 7.4;

II. More Polar Isomer

[α] $^{23}{}_D$ +21 (c 0.24, CHCl$_3$); IR (film) 3385, 2930, 1726, 1546, 1461, 1440, 1372, 1347, 1166, 909, 735, 581 cm$^{-1}$; $^1$HNMR (CDCl$_3$, 400 MHz) 8.56 (s, 1H), 7.98 (dd, J=7.7, 1.5 Hz, 1H), 7.76 (td, J=7.7, 1.5 Hz, 1H), 7.72 (td, J=7.7, 1.5 Hz, 1H), 7.64 (dd, J=7.7, 1.5 Hz, 1H), 7.50 (d, J=7.9 Hz, 1H), 7.33 (d, J=7.9 Hz, 1H), 7.16 (t, J=7.9 Hz, 1H), 7.08 (t, J=7.9 Hz, 1H), 4.15 (dd, J=10.0, 2.4 Hz, 1H), 4.02 (m, 1H), 3.70 (s, 3H), 3.58 (dd, J=10.8, 6.1 Hz, 1H), 3.54 (dd, J=10.8, 5.7 Hz, 1H), 3.40 (d, J=15.4 Hz, 1H), 3.31 (m, 3H), 2.77 (d, J=15.4 Hz, 1H), 2.44 (m, 1H), 2.17 (dt, J=13.9, 2.4 Hz, 1H), 1.80 (dt, J=13.9, 10.8 Hz, 1H), 1.05 (m, 4H), 0.40 (t, J=7.4 Hz, 3H); $^{13}$CNMR (CDCl$_3$, 100 MHz) 174.3, 149.0, 136.0, 134.1, 132.4, 131.5, 131.0, 130.3, 127.6, 124.2, 122.5, 119.8, 118.6, 111.1, 110.8, 73.0, 68.6, 61.8, 53.9, 52.5, 42.2, 37.5, 37.5, 36.0, 34.6, 25.6, 7.1;

The process to produce tosylate 21 by tosylation of diol 20 is mentioned below.

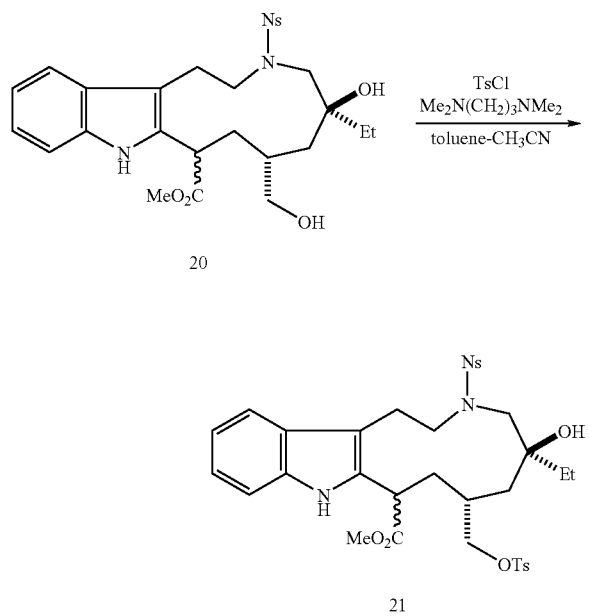

20

21

To a toluene-acetonitrile solution (1 mL-1 mL) of diol 20 (57.0 mg, 0.102 mmol) and tetramethyldiaminopropane (26 µL, 0.15 mmol) p-toluenesulfonly chloride (22 mg, 0.11 mmol) was added at room temperature and stirred for 3 hours. After solid was removed using Celite colume, the filtrate was concentrated in vacuo. The residue was refined by a silica gel column chromatography (30-50% ethyl acetate/n-hexane), and tosylate 21 (55 mg, 75%) was obtained as a yellowish oily product.

The characteristics of tosylate 21;

IR (film) 3514, 3393, 2956, 1728, 1595, 1546, 1461, 1440, 1354, 1173, 962, 754, 667, 580 cm$^{-1}$; $^1$HNMR (CDCl$_3$, 400 MHz) 8.67 (s, (½) 11), 8.51 (s, (112) 1H), 7.89 (d, J=8.0 Hz, (½) 1H), 7.81 (d, J=8.0 Hz, (112) 1H), 7.77 (d, J=8.0 Hz, (½) 2H), 7.73-7.57 (m, 4H), 7.43 (d, J=7.1 Hz, 1H), 7.36 (d, J=7.1 Hz, 1H), 7.32 (d, J=8.0 Hz, (½) 2H), 7.18 (t, J=7.1 Hz, (½) 1H), 7.16 (t, J=7.1 Hz, (½) 1H), 7.11 (d, J=8.0 Hz, (½) 2H), 7.06 (t, J=7.1 Hz, (½) 1H), 7.04 (t, J=7.1 Hz, (½) 1H), 4.23-4.07 (m, 2H), 3.92 (dd, J=9.5, 6.6 Hz, (½) 1H), 3.86 (dd, J=9.8, 7.1 Hz, (½) 1H), 3.80 (m, (½) 1H), 3.70 (s, (½) 3H), 3.69 (s, (½) 3H), 3.38 (d, J=15.0 Hz, 1H), 3.25 (m, 1H), 3.17 (m, (½) 1H), 3.10 (m, (½) 1H), 2.97 (d, J=15.0 Hz, (½) 1H), 2.63 (d, J=15.0 Hz, (½) 1H), 2.50 (m, (½) 1H), 2.42 (s, (½) 3H)<2.32 (s, (½) 3H, 2.21 (dt, J=13.9, 1.5 Hz, (½) 1H), 1.94 (d, J=15.9 Hz, (½) 1H), 1.83 (m, 1H), 1.49 (m, 2H), 1.28 (m, 2H), 1 02 (m, 2H), 0.77 (t, J=7.4 Hz, (½) 3H), 0.37 (t, J=7.4 Hz, (½) 3H);

The process to produce ester 22 contained in general formula A by the esterification of tosylate 21 with trifluoroacetic anhydride is mentioned below.

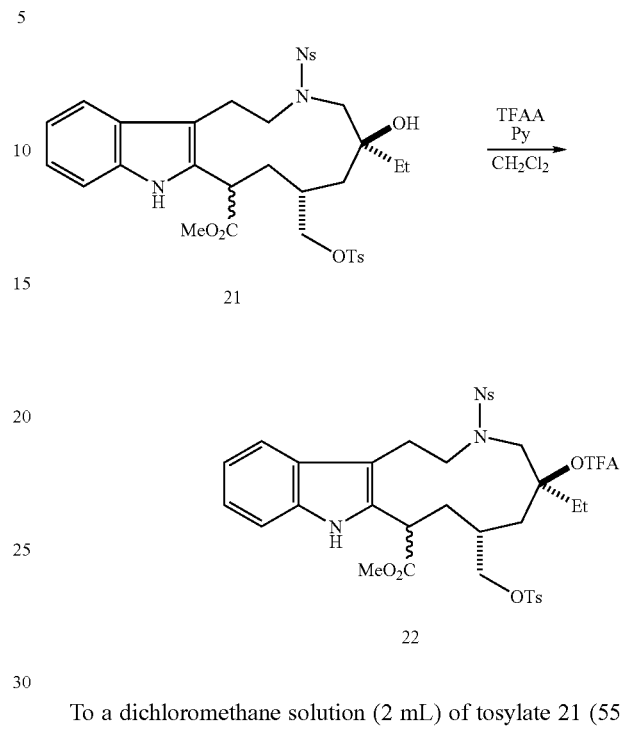

21

22

To a dichloromethane solution (2 mL) of tosylate 21 (55 mg, 0.077 mmol) and pyridine (62 µL, 0.77 mmol), trifluoroacetic anhydride (44 µL, 0.31 mmol) was added at room temperature and stirred for 1 hour. The saturated aqueous solution of sodium hydrogencarbonate was added to the reaction mixture, and after the organic layer was separated, the aqueous layer was extracted with ethyl acetate. The combined organic layer was washed with brine, and then dried over anhydrous sodium sulfate. After concentration in vacuo, the residue was refined by a silica gel column chromatography (20-40% ethyl acetate/n-hexane), and ester 22 (49 mg, 79%) was obtained as a light yellowish oily product.

The characteristics of ester 22;

IR (film) 3397, 2953, 1781, 1730, 1595, 1548, 1461, 1441, 1366, 1222, 1173, 965, 930, 817, 754, 667, 580, 556 cm$^{-1}$; $^1$HNMR (CDCl$_3$, 400 MHz), 8.74 (s, (½) 1H), 8.63 (s, (½) 1H), 7.93 (dd, J=7.3, 1.8 Hz, (½) 1H), 7.73 (m, 3H+ (½) 1H), 7.64 (dd, J=7.3, 1.8 Hz, (½) 1H), 7.58 (dd, J=7.3, 1.8 Hz, (½) 1H9, 7.53 (d, J=8.4 Hz, (½) 2H), 7.36 (m, 3H), 7.20 (t, J=7.4 Hz, (½) 1H), 7.18 (t, J=7.4 Hz, (½) 1H), 7.08 (t, J=7.4 Hz, (½) 1H), 7.06 (t, J=7.4 Hz, (½) 1H), 6.99 (d, J=8.4 Hz, (½) 2H), 4.49 (d, J=16.4 Hz, (½) 1H), 4.14 (m, 1H+(½) 1H), 4.05 (d, J=10.5 Hz, (½) 1H), 3.87 (m, 1H+(½) 1H), 3.74 (s, (½) 3H), 3.71 (s, (½) 3H), 3.38-3.08 (m, 3H), 2.78 (m, 1H), 2.64 (d, J=16.1 Hz, (½) 1H), 2.42 (s, (½) 3H), 2.25 (s, (½) 3H), 2.16 (m, 1H+ (½) 1H), 2.00 (d, J=14.2 Hz, (½) 1H), 1.90 (d, J=16.1 Hz, (½) 1H), 1.85-1.52 (m, 3H), 1.67 (brs, 1H), 1.02 (m, (½) 1H), 0.88 (t, J=7.4 Hz, (½) 1H), 0.77 (t, J=7.4 Hz, (½) 3H), 0.62 (d, J=15.6 Hz, (½) 1H), 0.25 (t, J=7.4 Hz, (½) 3H);

III The synthesis of (+)-vinblastines by coupling vindolines with the compound contained in general formula A synthesized in above mentioned II, then removing trifluoroacetyl group and Ns, further forming piperidine ring.

Example 3 a. The process to produce vinblastine precursor 23 contained in general formula E by coupling vindoline with ester 22 contained in general formula A is mentioned below.

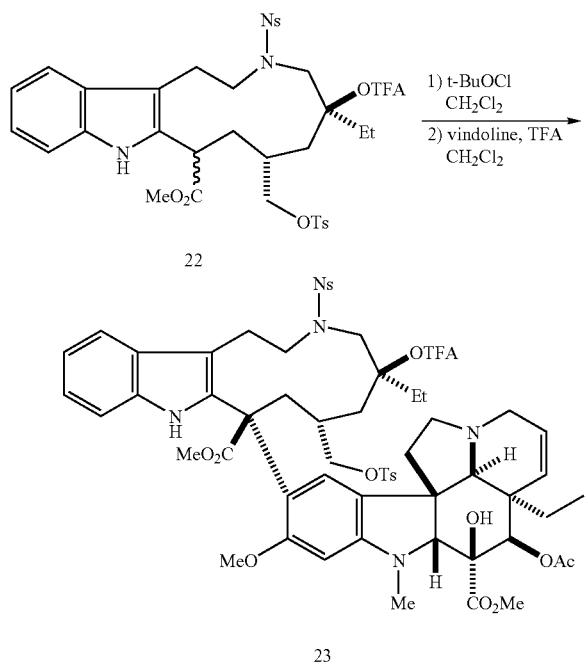

To a dichloromethane solution (0.4 mL) of ester 22 (10 mg, 0.012 mmol) cooled with ice, dichloromethane solution of t-butyl hypochrorite (1.5 μL, 0.013 mmol) was dropped and stirred for 15 minutes. The reaction mixture was refined directly by a silica gel thin layer chromatography and chloroindolenin was obtained. To a dichloromethane solution of the chloroindolenin and vindoline (5.6 mg, 0.012 mmol) cooled with ice, trifluoroacetic acid (10 μL, 0.12 mol) was added and stirred at the same temperature for 10 minutes and further stirred at room temperature for 20 minutes. The saturated aqueous solution of sodium hydrogencarbonate was added to the reaction mixture, and after the organic layer was separated, the aqueous layer was extracted with dichloromethane. The combined organic layer was dried over sodium sulfate, and then concentrated in vacuo. The residue was refined by a silica gel thin layer chromathography and the compound 23 (12.5 mg, 80.4%) was obtained as a colorless oily compound. The characteristics of compound 23;

$[\alpha]^{28}_D$+27 (c 0.32, CHCl$_3$); IR (film) 3414, 2952, 2879, 1778, 1740, 1614, 1548, 1498, 1461, 1434, 1396, 1226, 1175, 1043, 913, 817, 734, 668, 580, 554 cm$^{-1}$; $^1$HNMR (CDCl$_3$, 400 MHz) 10.56 (brs, 1H), 9.42 (brs, 1H), 7.86 (dd, J=7.8, 1.2 Hz, 1H), 7.78 (td, J=7.8, 1.2 Hz, 1H), 7.76 (d, J=8.3 Hz, 1H), 7.70 (td, J=7.8, 1.2 Hz, 1H), 7.64 (dd, J=7.8, 1.2 Hz, 1H), 7.41 (s, 1H), 7.34 (d, J=7.3 Hz, 1H), 7.32 (d, J=8.3 Hz, 2H), 7.14 (d, J=7.3 Hz, 1H), 7.11 (t, J=7.3 Hz, 1H), 6.94 (t, J=7.3 Hz, 1H), 5.91 (dd, J=10.2, 3.7 Hz, 1H), 5.81 (dd, J=10.2, 3.7 Hz, 1H), 5.57 (s, 1H), 5.27 (d, J=10.2 Hz, 1H), 4.12 (d, J=9.7 Hz, 1H), 3.90 (d, J=16.0 Hz, 1H), 3.80 (s, 3H), 3.79 (m, 1H), 3.71 (s, 3H), 3.64 (d, J=9.7 Hz, 1H), 3.44 (s, 3H), 3.44 (m, 1H), 3.36 (t, J=7.3 Hz, 1H), 3.29 (m, 1H), 3.16 (dd, J=16.0, 6.1 Hz, 1H), 3.04 (d, J=16.6 Hz, 1H), 2.94 (t, J=12.2 Hz, 1H), 2.82 (m, 2H), 2.81 (s, 1H), 2.70 (m, 1H), 2.63 (s, 3H), 2.54 (m, 2H), 2.41 (s, 3H), 2.09 (s, 3H), 1.89 (m, 3H), 1.71 (m, 2H), 1.58 (brs, 2H), 1.30 (m, 3H), 0.59 (t, J=7.4 Hz, 3H), 0.43 (t, J=7.3 Hz, 3H); $^{13}$CNMR(CDCl$_3$, 100 MHz) 177.1, 177.0, 172.3, 170.9, 158.5, 155.4, 155.0, 153.2, 148.8, 145.0, 135.1, 134.5, 134.0, 132.4, 131.6, 131.3, 130.2, 129.9, 128.0, 127.7, 127.7, 125.4, 124.6, 124.0, 122.5, 121.6, 120.1, 119.0, 117.5, 115.1, 112.2, 111.1, 108.4, 94.4, 94.1, 77.2, 72.9, 68.0, 55.7, 54.1, 53.0, 52.8, 52.6, 52.4, 51.0, 50.7, 43.4, 39.5, 37.8, 37.7, 31.6, 30.7, 29.3, 25.2, 21.6, 21.1, 8.8, 7.0;

The process to produce detrifluoroacetyl vinblastine precursor 24 from compound 23 is mentioned below.

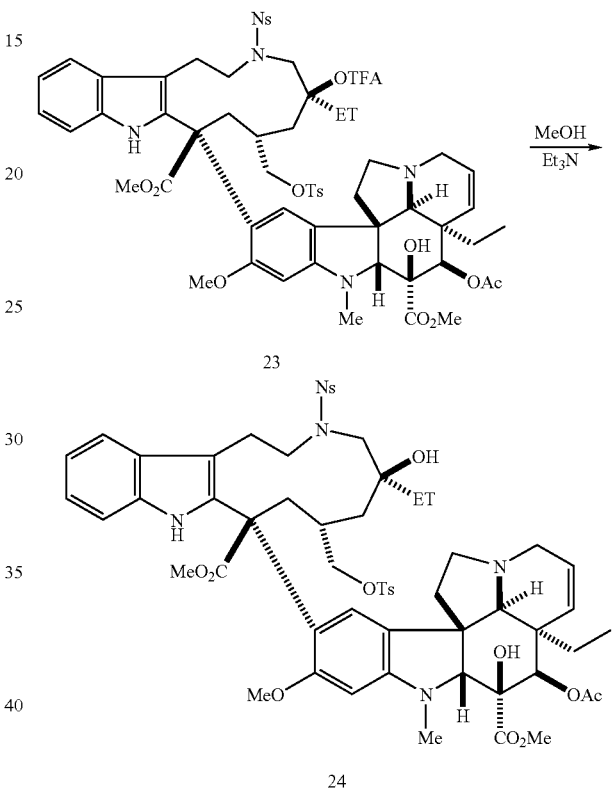

To the methanol solution (1 mL) of compound 23 (12.5 mg, 0.0100 mmol), triethylamine (12 μL) was dropped at room temperature and stirred for 45 minutes. After concentration in vacuo, compound 24 (10 mg, 90%) was obtained as a white solid.

The characteristics of compound 24;

$[\alpha]^{25}_D$+57 (c0.30, CHCl$_3$); IR (film) 3750, 3464, 3414, 2951, 1739, 1614, 1545, 1500, 1459, 1434, 1358, 1250, 1174, 1042, 964, 914, 837, 739, 667, 581, 556 cm$^{-1}$; $^1$HNMR (CDCl$_3$, 400 MHz) 10.99 (s, 1H), 7.83 (d, J=7.7 Hz, 1H), 7.79 (d, J=8.1 Hz, 2H), 7.75 (d, J=7.7 Hz, 1H), 7.68 (t, J=7.7 Hz, 2H), 7.58 (s, 1H), 7.43 (d, J=7.8 Hz, 1H), 7.34 (d, J=8.1 Hz, 2H), 7.19 (d, J=7.8 Hz, 1H), 7.17 (t, J=7.8 Hz, !H), 7.02 (t, J=7.8 Hz, 1H), 5.86 (s, 1H), 5.81 (dd, J=10.1, 4.4 Hz, 1H), 5.64 (s, 1H), 5.27 (d, J=10.1 Hz, 1H), 3.95 (dd, J=15.0, 5.6 Hz, 1H), 3.80 (s, 3H), 3.77 (s, 1H), 3.73 (dd, J=9.3, 6.6 Hz, 1H), 3.66 (d, J=9.3 Hz, 1H), 3.55 (s, 3H), 3.50 (m, 2H), 3.43 (s, 3H), 3.35 (m, 2H), 3.04 (m, 1H), 2.94 (s, 1H), 2.83 (m, 2H), 2.67 (m, 1H), 2.60 (s, 3H), 2.52 (dt, J=14.4, 4.4 Hz, 1H), 2.44 (s, 3H), 2.09 (s, 3H), 1.95 (dd, J=15.1, 9.8 Hz, 1H), 1.72 (dq, J=14.4, 7.3 Hz, 1H), 1.41 (d, J=14.9 Hz, 1H), 1.38-1.26 (m, 6H), 1.08 (dq, J=14.4, 7.3 Hz, 1H), 0.99 (dq, J=14.4, 7.3 Hz, 1H), 0.86 (m, 1H), 0.62 (t, J=7.3 Hz, 3H), 0.55 (t, J=7.3 Hz, 3H); $^{13}$CNMR (CDCl$_3$, 100 MHz) 176.7, 172.7, 171.0, 157.7, 153.4, 148.8, 144.8, 137.8, 134.1, 133.9, 132.9, 131.1, 130.5, 130.1, 129.8, 128.0, 127.4, 126.1, 124.8, 124.0, 122.6, 122.2, 120.8, 119.6, 117.3, 111.7, 106.7, 93.6, 83.3, 79.1, 76.2, 7.1, 73.4, 68.1, 64.6, 55.6, 54.1, 53.0, 52.8, 52.3, 52.2, 50.9, 50.3, 45.6, 43.6, 43.4, 40.1, 38.5, 37.7, 35.7, 31.6, 29.7, 29.0, 26.9, 21.6, 21.1, 9.1, 6.9;

The process to produce (+)-vinblastines by ring forming reaction of compound 24 is mentioned below.

Each instrument data were coincided with data in the literature (Reference Document I).

Abbreviation:
AIBN=azobisisobutyronitrile
Bn=benzyl
Boc=t-butoxycarbonyl group
DBU=1,8-diazabicyclo[5.4.0]undecene
DEAD=diethyl azodicarboxylate
DIBAL=diisobutylaluminum hydride
DMAP=4-dimethylaminopyridine

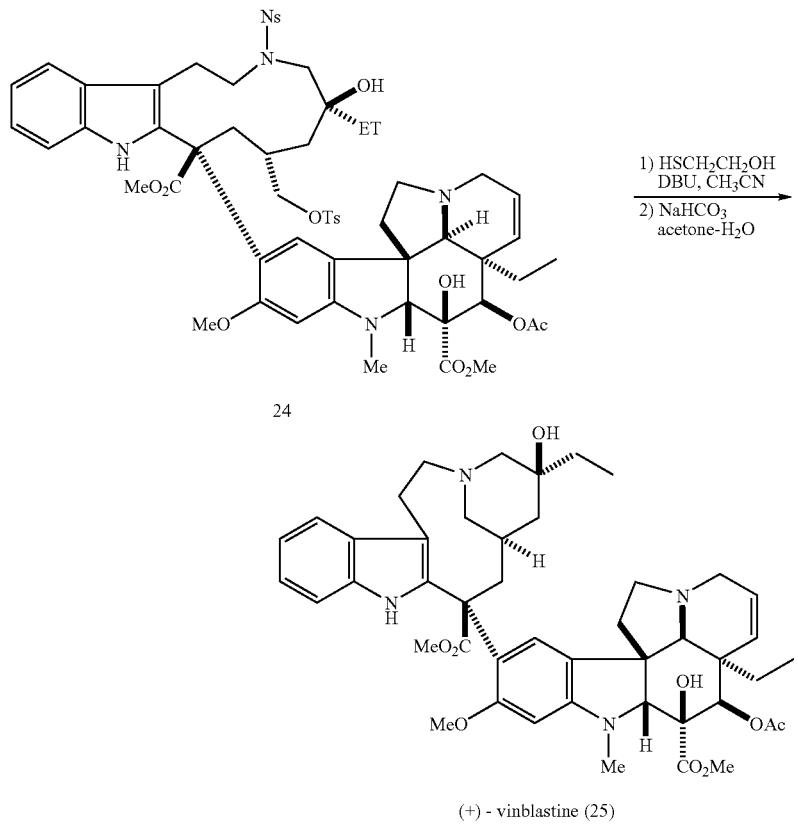

To the acetonitrile solution of the compound 24 (16 mg, 0.014 mmol) and 1,8-diazabicyclo[5.4.0] undecene (DBU) (3 µL, 0.02 mmol) cooled with ice, acetonitrile solution of mercaptoethanol (1 µL, 0.02 mmol) was dropped and stirred for 1 hour. The reaction mixture was partitioned between ethyl acetate and saturated aqueous solution of sodium hydrogencarbonate, and the aqueous layer was extracted with ethyl acetate. The combined organic layer was dried over anhydrous sodium sulfate and concentrated in vacuo. The residue was refined by a silica gel thin layer chromatography and a cyclization precursor (9.0 mg, 67%) was obtained as a yellowish oily product. To a acetone solution (0.3 mL) of the cyclization precursor (2.0 mg, 0.0020 mmol), saturated aqueous solution of sodium hydrogencarbonate (0.3 mL) was added and stirred for one night. The reaction mixture was partitioned between ethyl acetate and brine, and the aqueous layer was extracted with ethyl acetate. The combined organic layer was dried over anhydrous sodium sulfate and concentrated in vacuo. The residue was refined by a silica gel thin layer chromatography and vinblastine (25, 1.3 mg, 79%) was obtained as a white solid.

DMF=dimethylformamide
Et=ethyl group
LDA=lithium diisopropylamide
Me=methyl group
Ns=2-nitrobenzene sulfonyl
Ph=phenyl group
Py=pyridine
TBDPS=t-butyldiphenylsilyl
TES=triethylsilyl group
TFA=trifluoroacetyl group or trifluoroacetic acid
TFAA=trifluoroacetic anhydride
THF=tetrahydrofuran
THP=tetrahydropyranyl group
TMS=trimethylsilyl group
Ts=p-tosyl group

REFERENCE DOCUMENTS

A;
Noble, R. L.; Beer, C. T.; Cutts, J. H. Ann. N.Y. Acad. Sci. 1958, 76, 882.

B;
Blasko, G.; Cordell, G. A.; Kuehne, M. E.; Marko, I.; Borman, L. S.; Pearce, H. L.; McCormack, J. J. Neuss, N.; Neuss, M. N. The Alkaloids; Brossi, A.; Suffness, M., Ed.; Academic Press: New York, 1990; Vo137.
C;
Kutney, J. P.; Beck, J.; Bylsma, F.; Cook, J.; Cretney, W. J.; Fuji, K.; Imhof, R.; Treasurywala, A. M. Hwlv. Chim. Acta 1975, 58, 1690.
D;
Schill, G.; Priester, C. U.; Windhovel, U. F.; Fritz, H. Helv. Chim. Acta 1986, 69, 438.
E
Tokuyama, H.; Yamashita, T.; Reding, M. T.; Kaburagi, Y; Fukuyama, T. J. Am. Chem. Soc. 1999, 121, 3791.
F;
Fujiwara, A.; Kan.; T. Fukuyama, T. Synlett 2000, 1667.
G;
Martinelli, M. J.; Nayyar, N. K.; Moher, E. D.; Dhokte, U. P.; Pawlak, J. M.; Vaidyanathan, R. Org. Lett. 1999, 1, 447.
H;
Yoshida, Y; Shimonishi, K.; Sakakura, Y.; Okada, S.; Aso, N.; Tanabe, Y Synthesis 1999, 1633.
I;
a) Kuehne, M. E.; Matson, P. A.; Bornmann, W. G. J. Org. Chem. 1991, 56, 513.
b) Magnus, P.; Mendoza, J. S.; Stamford, A.; Ladlow, M.; Willis, P. J. Am. Chem. Soc. 1992, 114, 10232.
J;
Men, J. L.; Taylor, W. I. Experientia 1965, 21, 598.

INDUSTRIAL APPRICABILITY

As mentioned above, by way of an intermediate represented by general formula A of the present invention, the coupling reaction of two indole compounds and followed forming reaction of indole ring progress streoselectively and effectively and natural type vinblastines can be obtained with high efficiency. Further, an excellent effect, that the production of said precursor can be performed under mild conditions, is provided by the present invention.

The invention claimed is:

1. A method for synthesis of (+)-vinblastines represented by formula F formula F

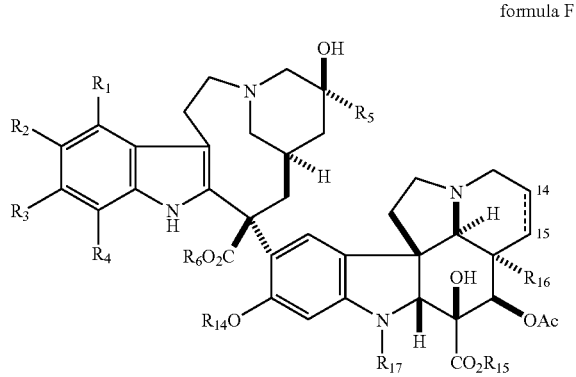

wherein $R_1$, $R_2$, $R_3$ and $R_4$ are the group selected independently from the group consisting of H, lower alkyl group, lower alkoxy group, halogen, lower perfluoroalkyl group, lower alkylthio group, hydroxy group, amino group, mono- or di-alkyl or acylamino group, lower alkyl or arylsulfonyloxy group, $R_5$ is H, or a lower alkyl group or a substituted or non-substituted aryl group, $R_6$ is an alkyl group of carbon number 4 or less, $R_{14}$, $R_{15}$ and $R_{16}$ are an alkyl group of carbon number 4 or less, $R_{17}$ is H or an alkyl group of carbon number 4 or less, and in between carbon 14 and carbon 15 is an unsaturated double bond or saturated bond, comprising, chlorination of 3 site of indole by treating indole derivatives of formula A with t-butylhypochlorite,

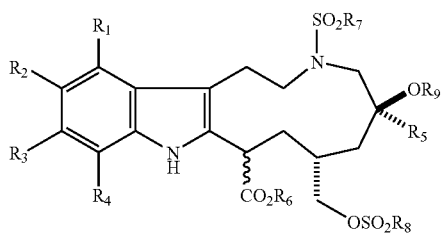

wherein $R_1$, $R_2$, $R_3$, $R_4$, $R_5$, and $R_6$ have the same meaning as in formula F, $R_7$ is a substituted or non-substituted aryl group, $R_8$ is a substituted or non-substituted aryl group or lower alkyl group and $R_9$ is an acyl group or trialkylsilyl group, preparing the compound of formula E by coupling of vindolines by the treatment of the obtained chlorinated product with trifluoroacetic acid under the presence of vindolines, then removing trifluoroacetyl group and $SO_2R_7$, and forming a piperidine ring, formula E

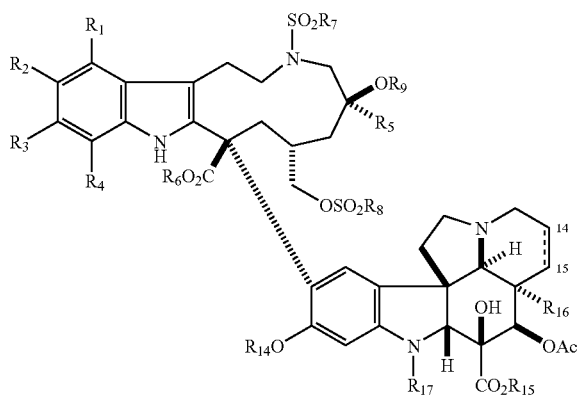

wherein $R_1$, $R_2$, $R_3$, $R_4$, $R_5$, and $R_6$, have same meaning to the case of formula F; $R_7$, $R_8$, and $R_9$, have same meaning to the case of formula A; and $R_{14}$, $R_{15}$, $R_{16}$, and $R_{17}$ have same meaning to the case of formula F, and in between carbon 14-carbon 15 is an unsaturated double bond or saturated bond.

* * * * *